United States Patent
Huo et al.

(10) Patent No.: US 12,168,645 B2
(45) Date of Patent: Dec. 17, 2024

(54) PHENANTHROIMIDAZOLE DERIVATIVE, AND PREPARATION METHOD THEREFOR AND APPLICATION THEREOF

(71) Applicant: GUANGDONG UNIVERSITY OF TECHNOLOGY, Guangdong (CN)

(72) Inventors: Yanping Huo, Guangdong (CN); Yudong Wen, Guangdong (CN); Hongping Xiang, Guangdong (CN); Shaomin Ji, Guangdong (CN); Wencheng Chen, Guangdong (CN); Jiye Luo, Guangdong (CN); Liang Gao, Guangdong (CN); Jingwei Zhao, Guangdong (CN)

(73) Assignee: GUANGDONG UNIVERSITY OF TECHNOLOGY, Guangdong (CN)

( * ) Notice: Subject to any disclaimer, the term of this patent is extended or adjusted under 35 U.S.C. 154(b) by 0 days.

(21) Appl. No.: 18/558,188

(22) PCT Filed: Jul. 30, 2021

(86) PCT No.: PCT/CN2021/109699
§ 371 (c)(1),
(2) Date: Oct. 30, 2023

(87) PCT Pub. No.: WO2023/284022
PCT Pub. Date: Jan. 19, 2023

(65) Prior Publication Data
US 2024/0239754 A1    Jul. 18, 2024

(30) Foreign Application Priority Data
Jul. 13, 2021  (CN) .......................... 202110792199.6

(51) Int. Cl.
| | | |
|---|---|---|
| *C07D 235/02* | (2006.01) | |
| *C07D 403/10* | (2006.01) | |
| *C07D 403/14* | (2006.01) | |
| *C07D 405/10* | (2006.01) | |
| *C07D 409/10* | (2006.01) | |
| *C07D 413/10* | (2006.01) | |

(Continued)

(52) U.S. Cl.
CPC ......... *C07D 235/02* (2013.01); *C07D 403/10* (2013.01); *C07D 403/14* (2013.01); *C07D 405/10* (2013.01); *C07D 409/10* (2013.01); *C07D 413/10* (2013.01); *C07D 417/10* (2013.01); *C08F 2/48* (2013.01)

(58) Field of Classification Search
CPC .. C07D 235/02; C07D 403/10; C07D 405/10; C07D 409/10; C07D 413/10; C07D 417/10; C07D 403/14
USPC ..................................................... 548/302.7
See application file for complete search history.

(56) References Cited

U.S. PATENT DOCUMENTS

| | | |
|---|---|---|
| 4,770,976 A | 9/1988 | Loerzer et al. |
| 4,857,438 A | 8/1989 | Loerzer et al. |

FOREIGN PATENT DOCUMENTS

| | | |
|---|---|---|
| CN | 104592125 | 5/2015 |
| CN | 104650041 | 5/2015 |

(Continued)

OTHER PUBLICATIONS

"International Search Report (Form PCT/ISA/210) of PCT/CN2021/109699", mailed on Apr. 13, 2022, with English translation thereof, pp. 1-5.

(Continued)

*Primary Examiner* — Kahsay Habte
(74) *Attorney, Agent, or Firm* — JCIPRNET

(57) ABSTRACT

Provided are a phenanthroimidazole derivative, and a preparation method therefor, and an application thereof. The phenanthroimidazole derivative has a structural formula as shown in Formula (I), R being an electron donor group,

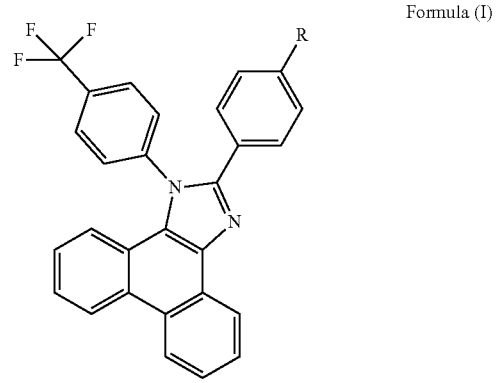

Formula (I)

wherein by taking a phenanthroimidazole group containing a trifluoromethyl phenyl group as an electron acceptor, and in virtue of the properties of the specific electron donor group R, the phenanthroimidazole derivative containing a light-absorbing photosensitive group of a series D-π-A structure is synthesized, and can be used as a photoinitiator, which is used in the technical field of UV light-curing systems or 3D printing. The phenanthroimidazole derivative has a certain conjugated chain length, can increase its photon absorption cross section, can serve as a photoinitiator of a UV light-curing system, for initiating a polymerization reaction at a wavelength of 365 nm, and has high polymerization efficiency; a double bond conversion rate of the phenanthroimidazole derivative in 50 s is up to 88.34%.

6 Claims, 11 Drawing Sheets

(51) Int. Cl.
*C07D 417/10* (2006.01)
*C08F 2/48* (2006.01)

(56) References Cited

FOREIGN PATENT DOCUMENTS

| CN | 106349213 | 1/2017 |
| CN | 112979649 | 6/2021 |

OTHER PUBLICATIONS

Huang Zhi et al., "Highly Twisted Bipolar Emitter for Efficient Nondoped Deep-Blue Electroluminescence," Dyes and Pigments, vol. 140, Jan. 2017, pp. 1-41.

PHENANTHROIMIDAZOLE DERIVATIVE, AND PREPARATION METHOD THEREFOR AND APPLICATION THEREOF

CROSS-REFERENCE TO RELATED APPLICATION

This is a 371 application of the International PCT application serial no. PCT/CN2021/109699, filed on Jul. 30, 2021, which claims the priority benefits of China Application Ser. No. 202110792199.6, filed on Jul. 13, 2021. The entirety of each of the above-mentioned patent applications is hereby incorporated by reference herein and made a part of this specification.

BACKGROUND

Technical Field

The present invention is in the field of UV light curing and particularly relates to a phenanthroimidazole derivative, and a preparation method therefor and an application thereof.

Description of Related Art

Ultraviolet (UV) light curing technology is an environment-friendly green technology in the fields of coatings, inks, adhesives, and so on. Compared with traditional solvent-containing systems, UV light curing technology has the outstanding characteristics of solvent-free emission, high efficiency, energy saving, and so on. Host materials in UV light curing are generally composed of oligomers, monomers, and photoinitiators, all cured under the action of sufficient UV light. As UV light-curing materials are more and more widely used, some problems of photoinitiator migration occur. However, by introducing large molecular weight groups, the migration problem of the photoinitiator can be effectively reduced, so that the residue of the initiator is small and no migration problem is achieved. For example, oxime ester photoinitiator OEX-2 is a kind of UV photoinitiator that has been widely studied in recent years. In addition, for example, Chinese patent CN106349213A discloses a hydrogen self-supply type photoinitiator and a preparation method thereof, wherein a photosensitive group is introduced into the photoinitiator, which can not only improve the photosensitivity of the initiator, enhance the light absorption capacity of the initiator, cause a significant red shift in the absorption spectrum of the initiator, but also improve the thermal stability of the initiator.

The design and synthesis of new photoinitiators containing photosensitive groups has become one of the hot spots in the field of photo-curing technology in recent years.

SUMMARY

It is an object of the present invention to provide a phenanthroimidazole derivative that can be used as a photoinitiator. In the present invention, wherein by taking a phenanthroimidazole group containing a trifluoromethyl phenyl group as an electron acceptor, and in virtue of the properties of the specific electron donor group R, the phenanthroimidazole derivative containing a light-absorbing photosensitive group of a series D-π-A structure is synthesized, and can be used as a photoinitiator, which is used in the technical field of UV light-curing systems or 3D printing. The phenanthroimidazole derivative has a certain conjugated chain length, can increase its photon absorption cross section, can serve as a photoinitiator of a UV light-curing system, for initiating a polymerization reaction at a wavelength of 365 nm, and has high polymerization efficiency.

It is another object of the present invention to provide a preparation method for the above phenanthroimidazole derivatives.

It is a further object of the present invention to provide the use of the above phenanthroimidazole derivatives in the preparation of UV light-curing initiators.

In order to solve the above technical problem, the present invention adopts the following technical solutions:

A phenanthroimidazole derivative having a structural formula as shown in Formula (I):

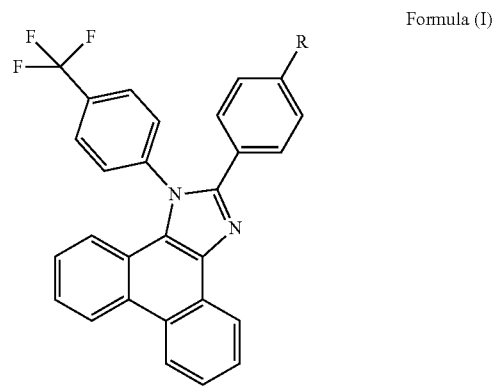

Formula (I)

in the Formula (I), R is an electron donor group, R is selected from the group consisting of a benzo five-membered unsaturated heterocyclic group, a substituted or unsubstituted dibenzo five-membered ring group, a substituted or unsubstituted dibenzo five-membered heterocyclic group, a group formed by at least two dibenzo five-membered heterocycles connected to a heteroatom in a dibenzo five-membered heterocycle through a carbon atom on a benzene ring in the dibenzo five-membered heterocycle and the dibenzo five-membered heterocycle is substituted or unsubstituted, a group formed by at least two dibenzo five-membered heterocycles connected to the same benzene ring through a heteroatom in the dibenzo five-membered heterocycle, a heteroanthracene group, a heteroanthracene group which is mono-or polysubstituted by methyl on a carbon atom of a six-membered heterocycle, a group formed by connecting two heteroanthracenes through a carbon atom of the six-membered ring in the heteroanthracene, or a substituted aniline group;

wherein the heteroatoms in the above groups are independently selected from one of or a combination of S, O, and N; the substituted groups are independently selected from methyl, phenyl, methoxy, methoxyphenyl, or tert-butylphenyl.

It should be noted that the above-mentioned substitution may be a single substitution or a multiple substitution, and theoretically, the sites where the substitution may occur may be substituted; the number of substituent groups is preferably 1 to 4.

In the above groups, the electron donor group R may be bound to the electron acceptor through a heteroatom or a carbon atom.

The phenanthroimidazole derivatives known from the prior art are generally used in the pharmaceutical field or as luminescent materials, in particular blue light materials, in electronic products.

The present inventors have inventively found that the substitution modification of the two positions C2 and N1 of phenanthroimidazole (structural formula:

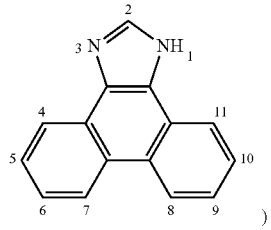 [SMILES: c1ccc2c(c1)c1ccccc1c1[nH]cnc21]

)

has an important effect on the properties of the material, in particular, the modification group at the C2 position has an important effect on the conjugation length of the whole molecule and determines the light absorption/emission properties of the derivative, for example, the modification of the phenyl group at the C2 position and the attachment of a specific electron donor group can increase the photon absorption cross-section of the compound and increase the absorption range by virtue of the properties of the specific electron donor group R; in addition, phenanthroimidazole derivatives with D-π-A (Doner-π-Accepter) structure were prepared by using phenanthroimidazole derivative containing trifluoromethyl phenyl group as electron acceptors. The trifluoromethyl group in the electron acceptors has antioxidant and solubilizing effects to enhance the polymerization effect. The phenanthroimidazole derivatives work together with iodonium salts to initiate polymerization at 365 nm wavelength with high polymerization efficiency.

Preferably, the benzo five-membered unsaturated heterocyclic group is

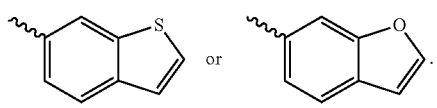

Preferably, the substituted or unsubstituted dibenzo five-membered ring-like group is

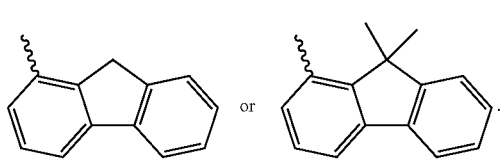

Preferably, the substituted or unsubstituted dibenzo five-membered heterocyclic group is

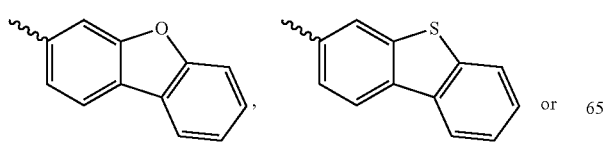

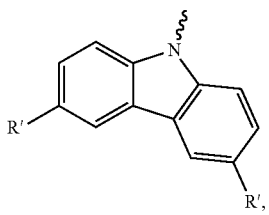

is wherein R' is independently selected from H or t-Bu.

Preferably, the group formed by at least two dibenzo five-membered heterocycles connected to a heteroatom in a dibenzo five-membered heterocycle through a carbon atom on a benzene ring in the dibenzo five-membered heterocycle is

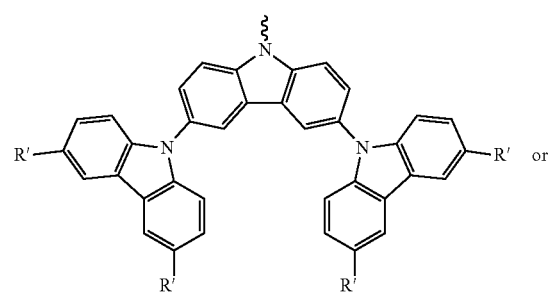

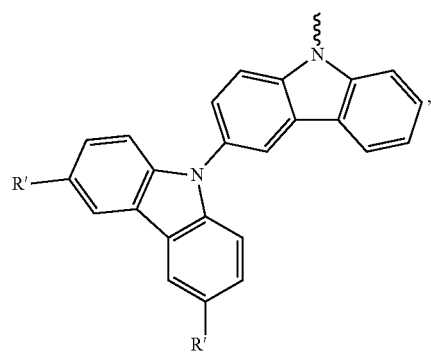

wherein R' is independently selected from H or t-Bu.

Preferably, the group formed by at least two dibenzo five-membered heterocycles connected to the same benzene ring through a heteroatom in the dibenzo five-membered heterocycles is

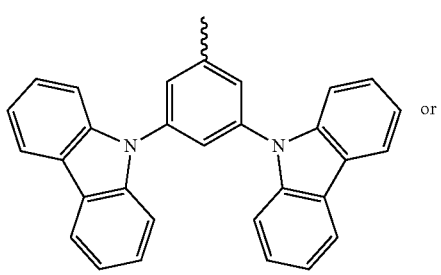

-continued

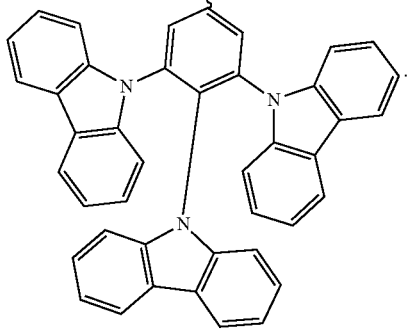

Preferably, the heteroanthracene group is

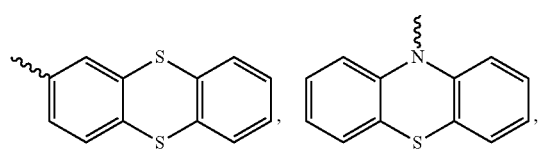

or

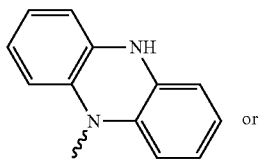

Preferably, the heteroanthracene group mono- or polysubstituted at a carbon atom of the six-membered heterocycle with a methyl group is

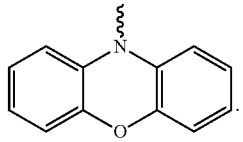

Preferably, the group in which the two heteroanthracenes are connected through a carbon atom on the six-membered ring in the heteroanthracene is

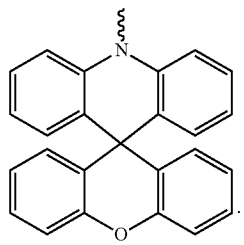

Preferably, the substituted aniline group is

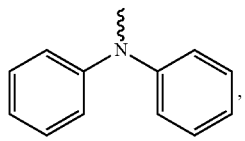

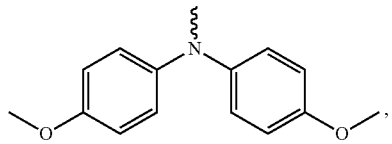

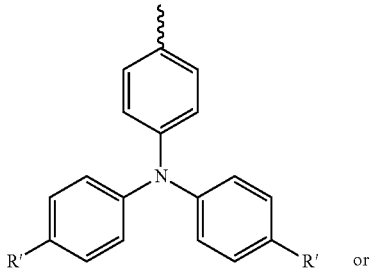

or

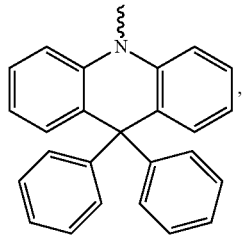

wherein R' is independently selected from H or t-Bu.

Preferably, the phenanthroimidazole derivative has the following structural formulae:

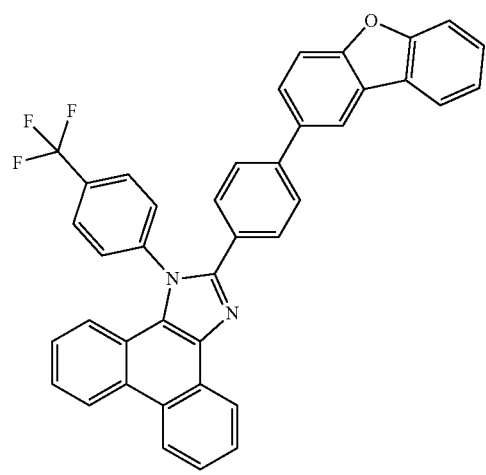
A1
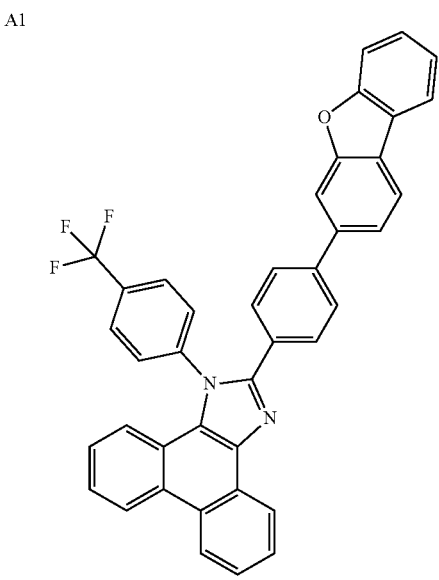
A2
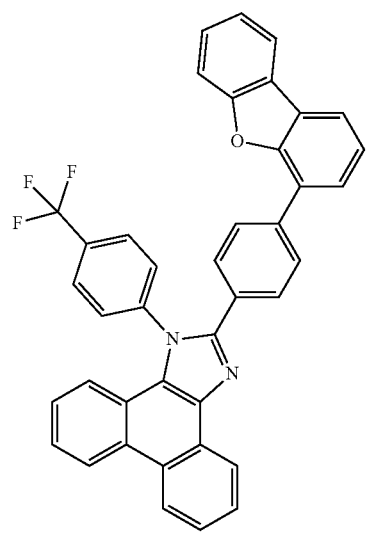
A3
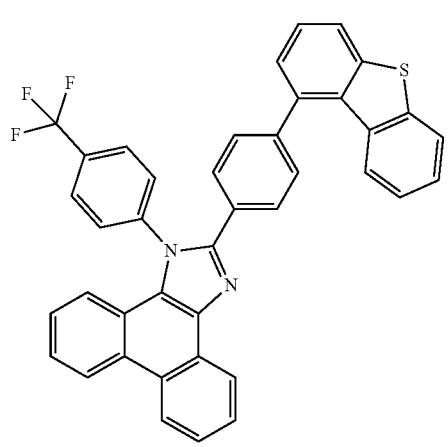
A4
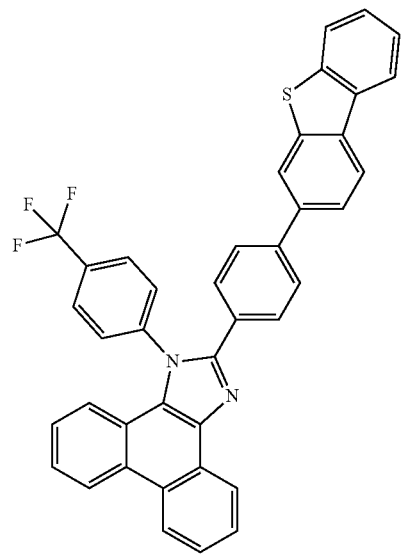
A5
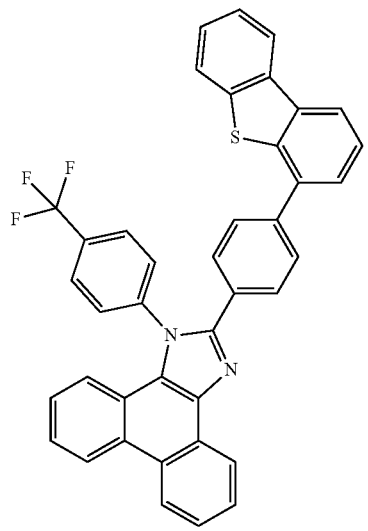
A6

-continued
| | |
|---|---|
| A7 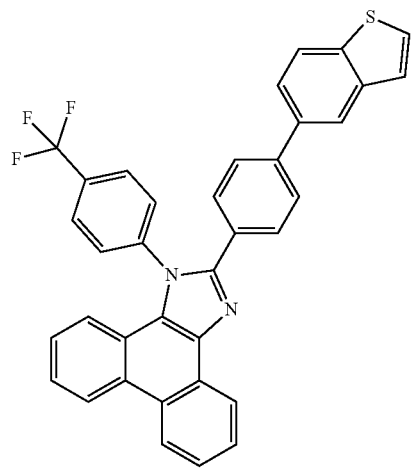 | A8 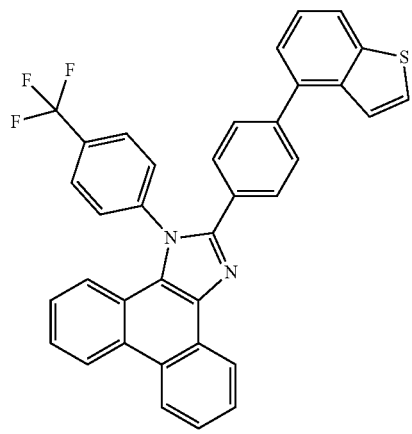 |
| A9 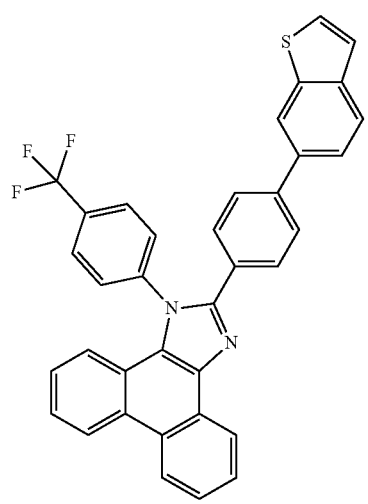 | A10 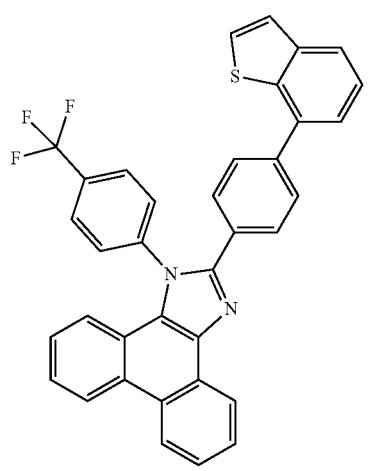 |
| A11 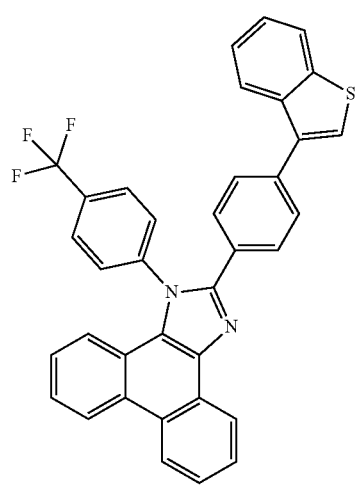 | A12 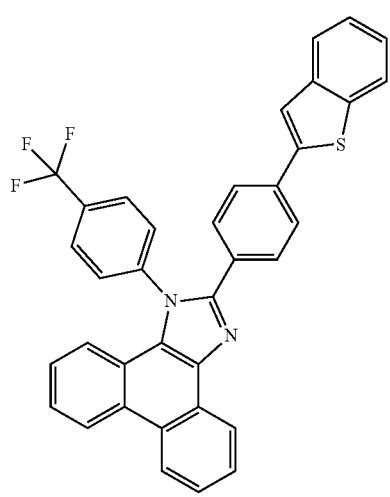 |

-continued
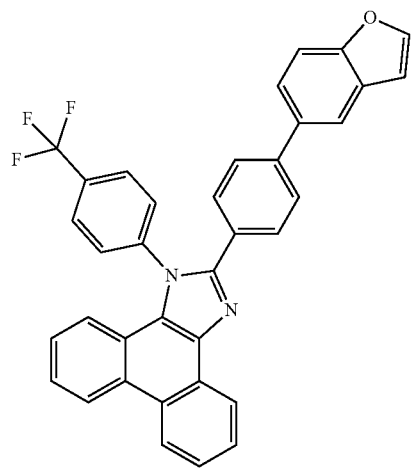
A13
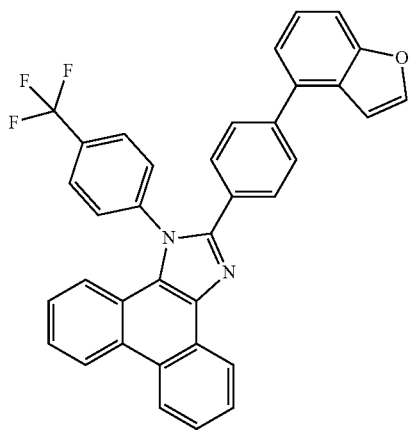
A14
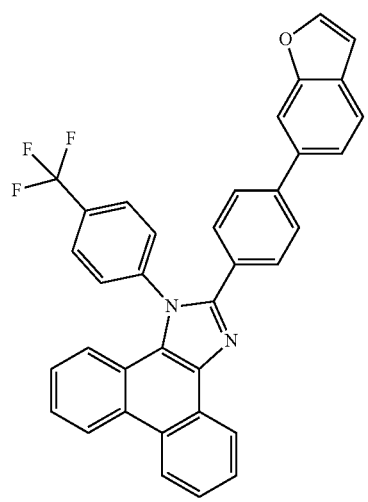
A15
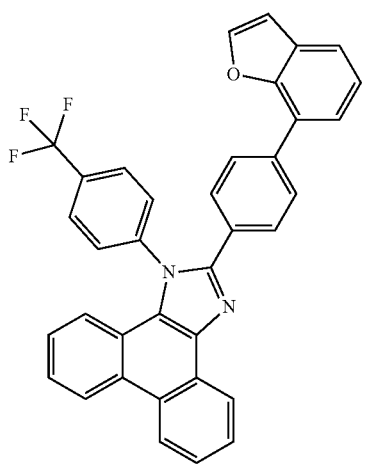
A16
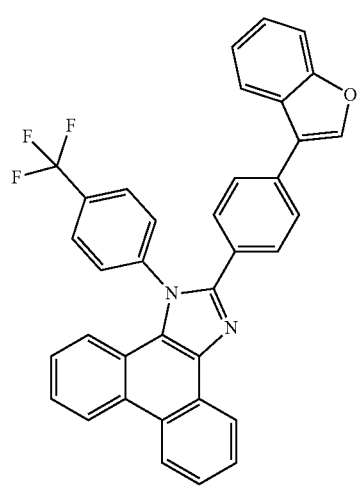
A17
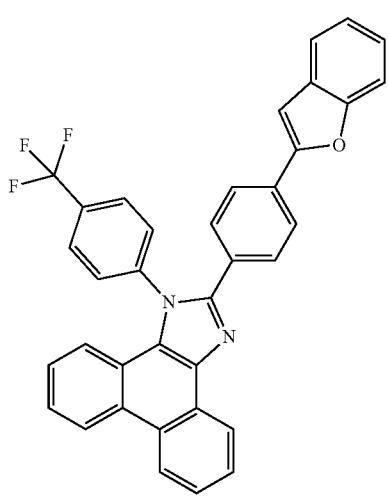
A18

-continued
A19
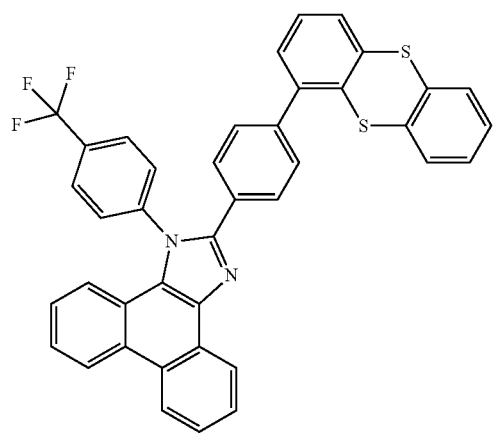
A20
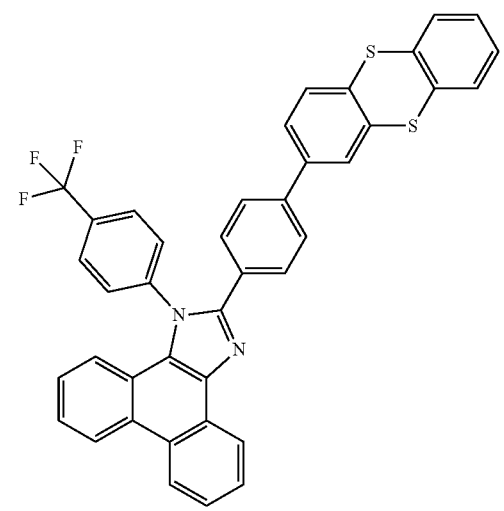
A21
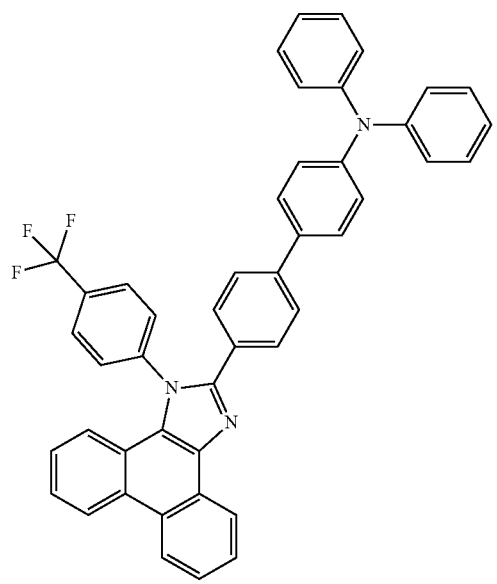
A22
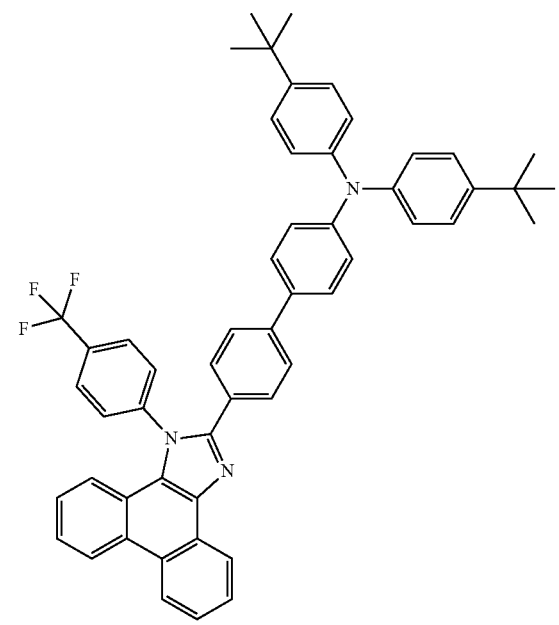
A23
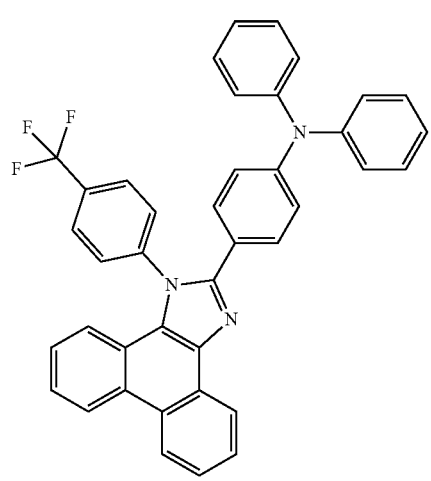
A24
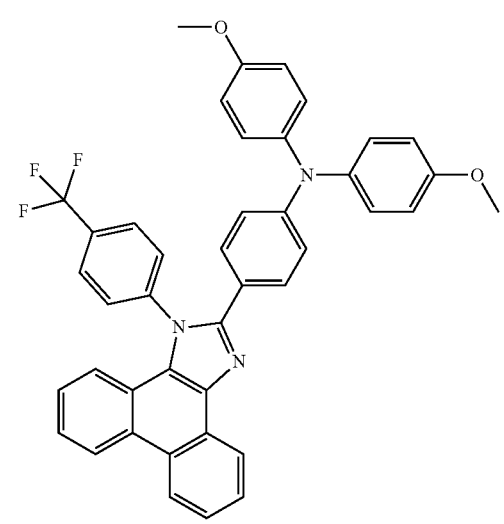

-continued
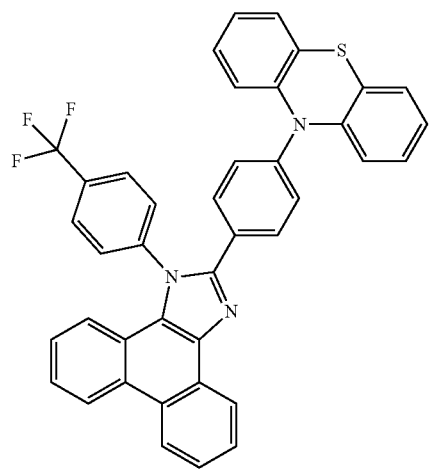
A25
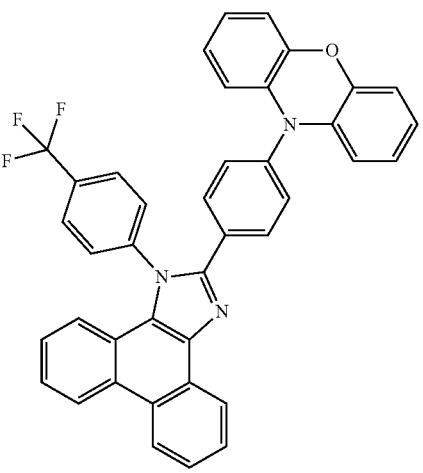
A26
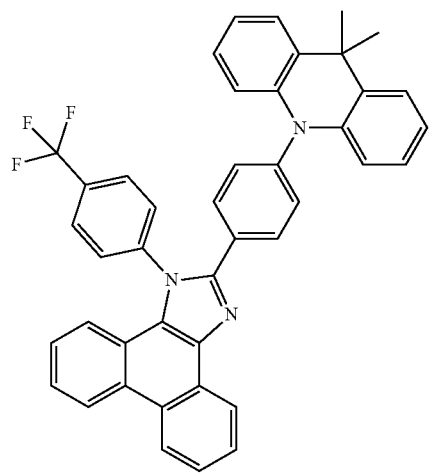
A27
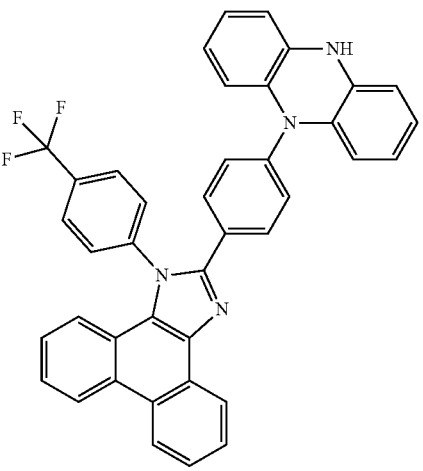
A28
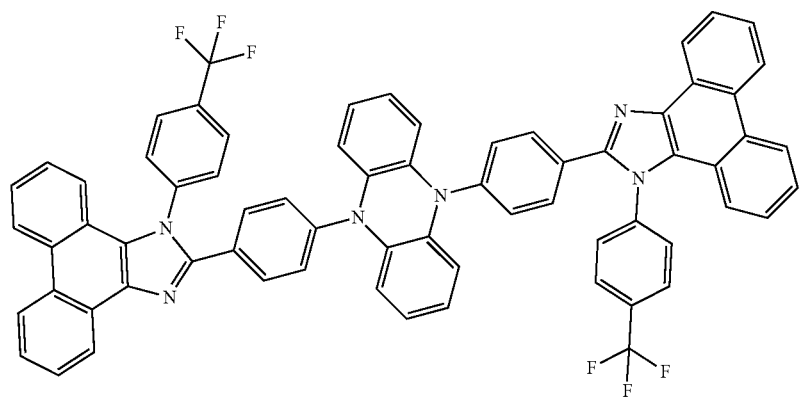
A29

-continued
A30
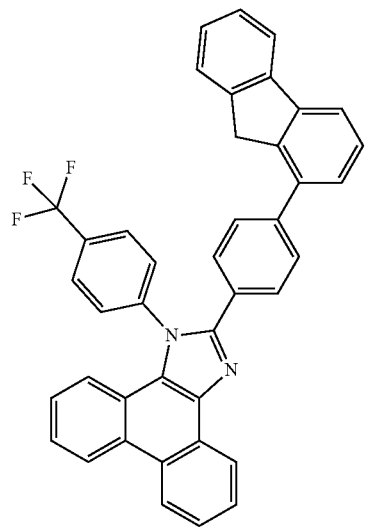
A31
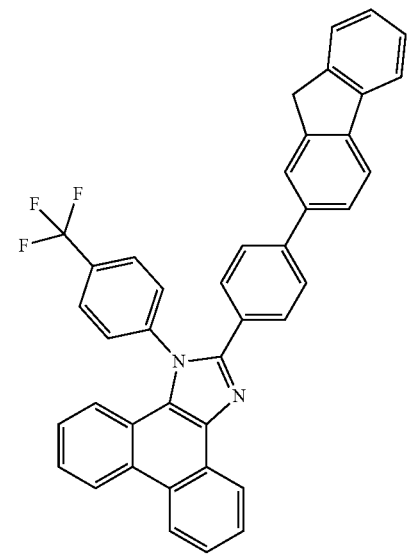
A32
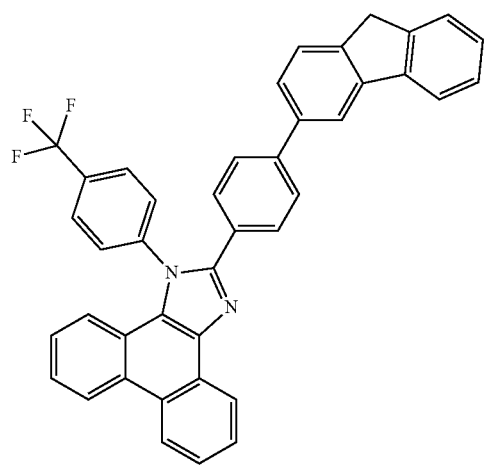
A33
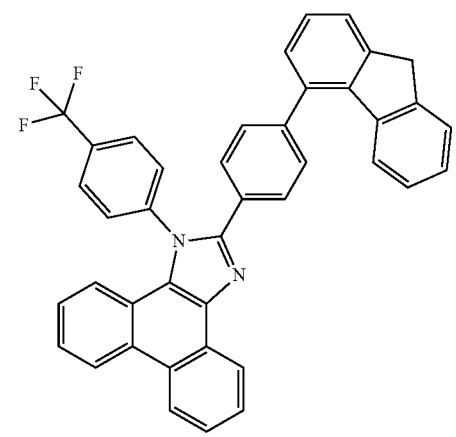
A34
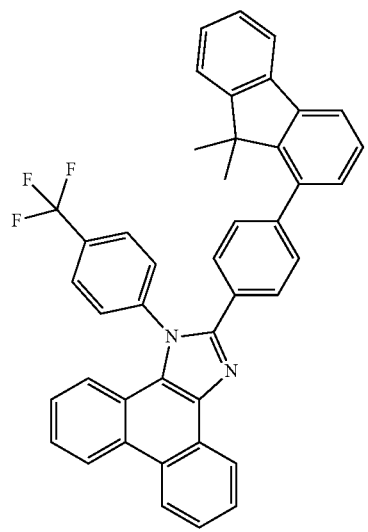
A35
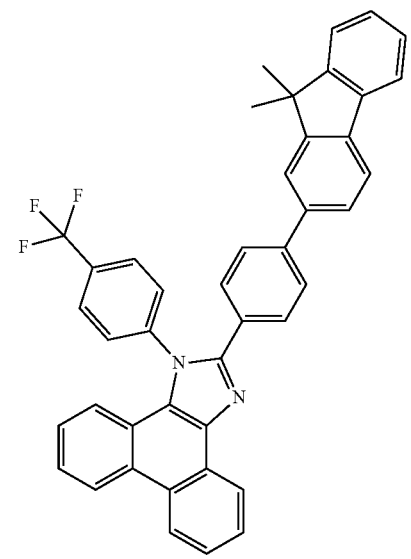

-continued
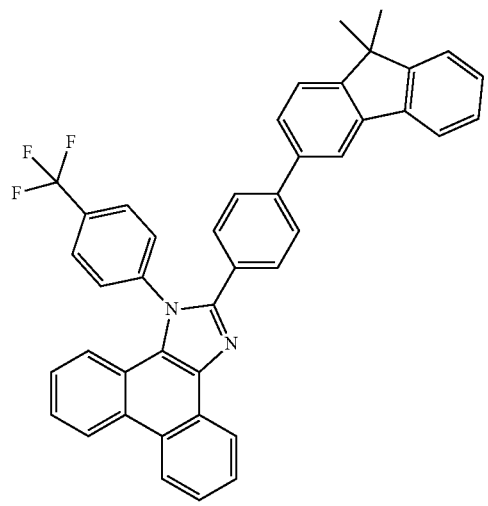
A36
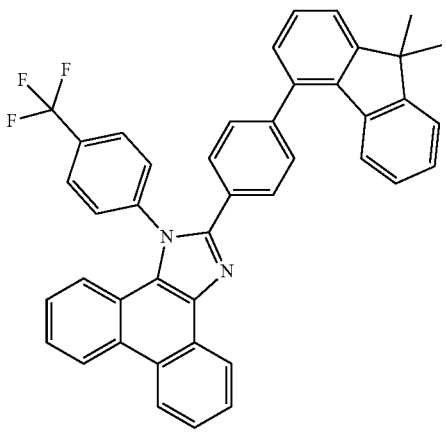
A37
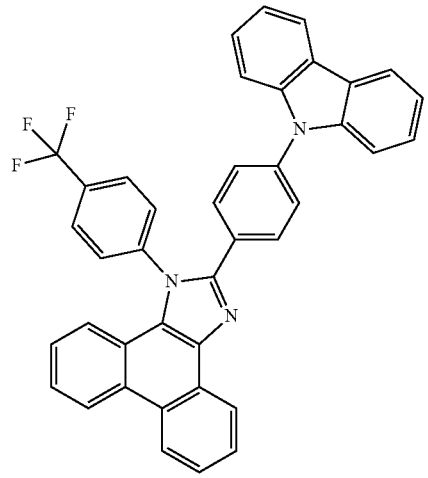
A38
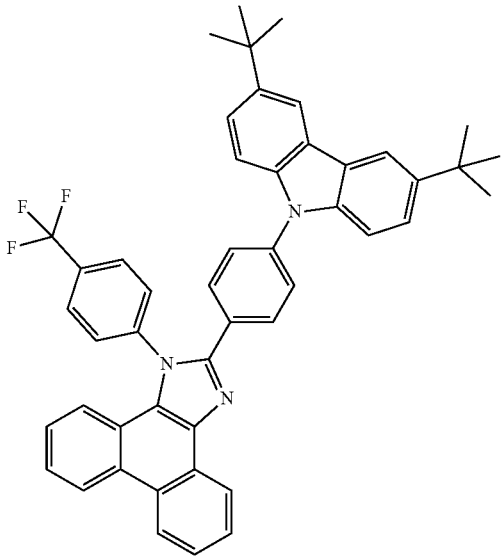
A39
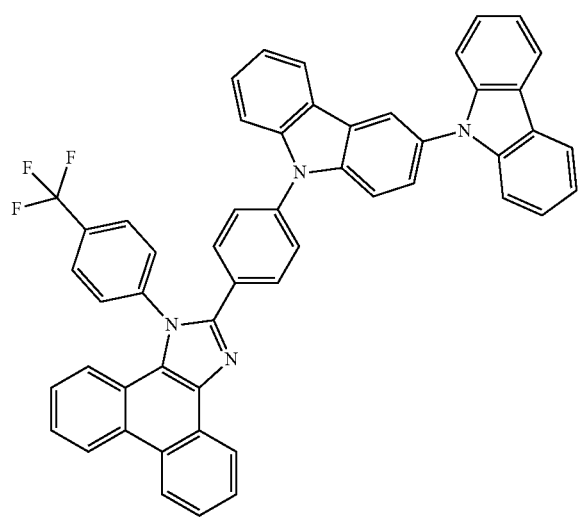
A40
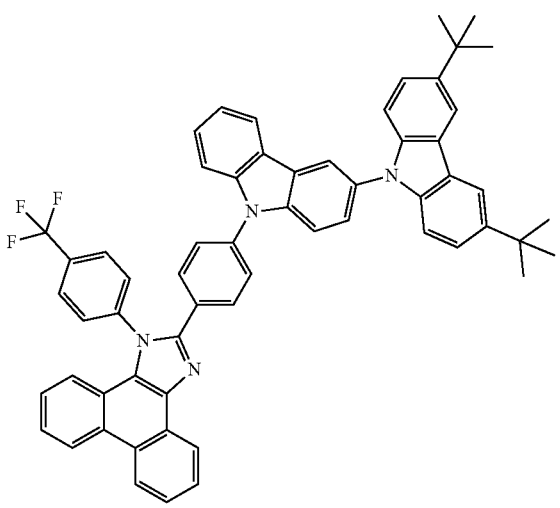
A41

-continued
A42
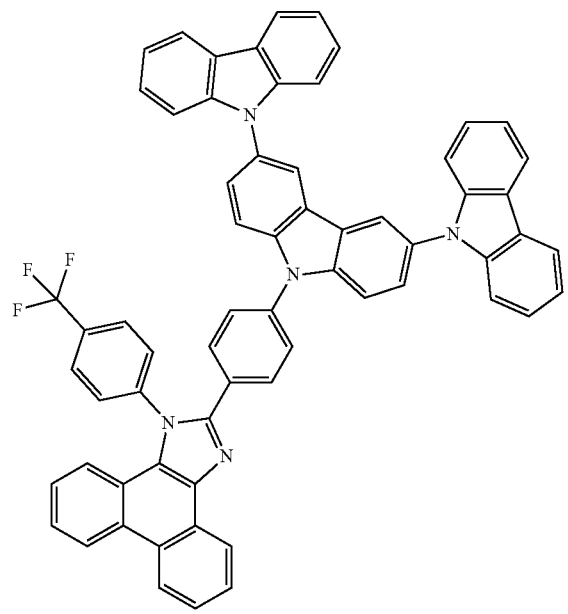
A43
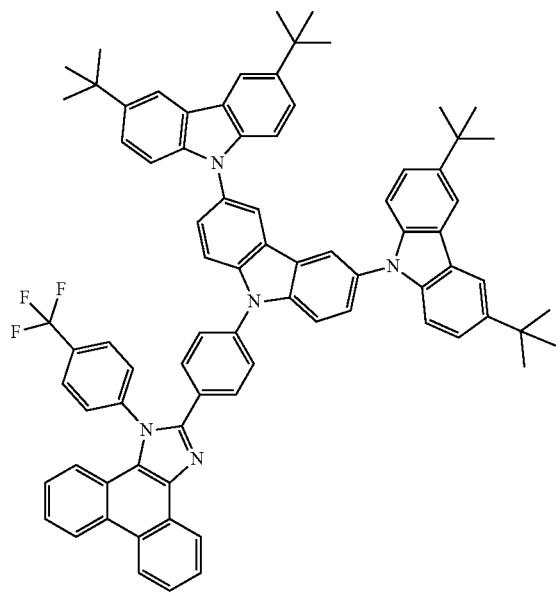
A44
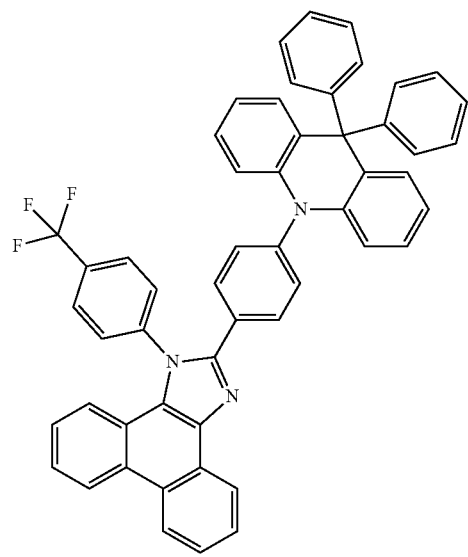
A45
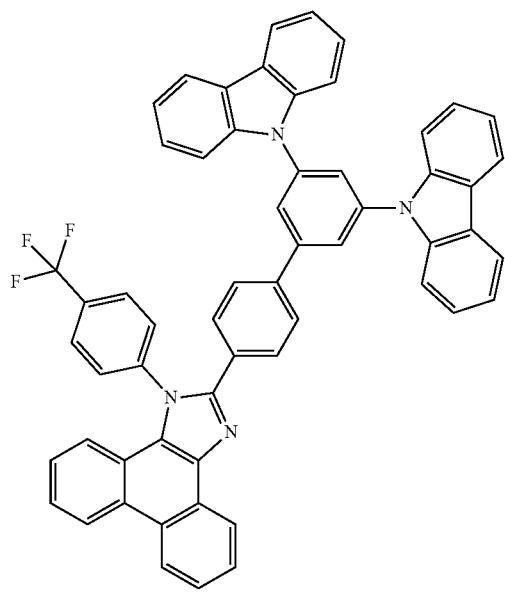

A46
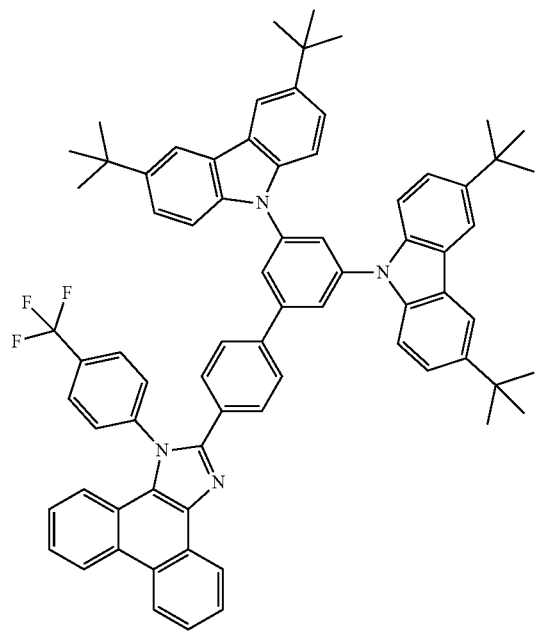
A47
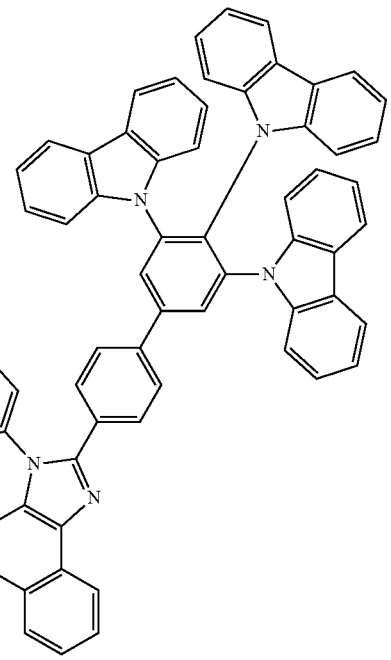
A48
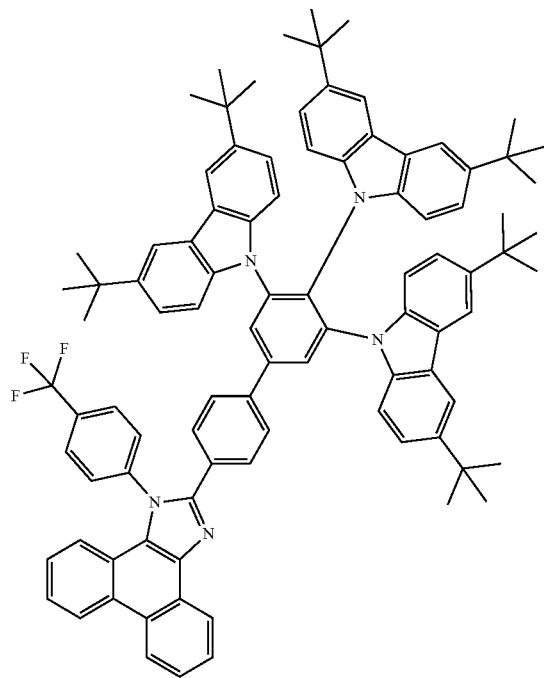
A49
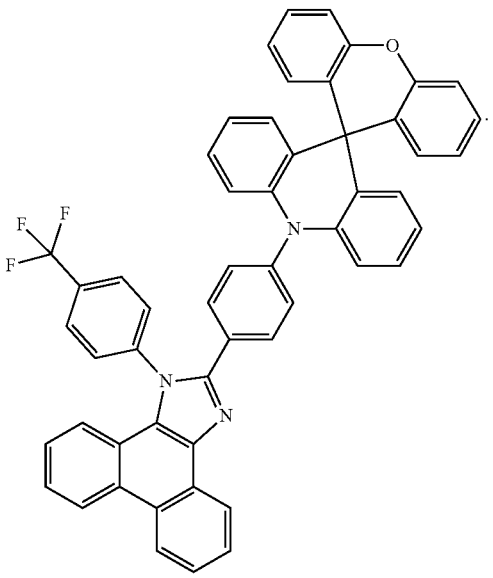

Further preferably, the phenanthroimidazole derivative has the following structural formulae:
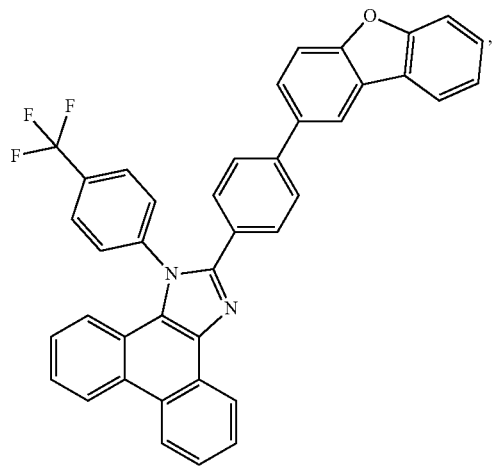
A1
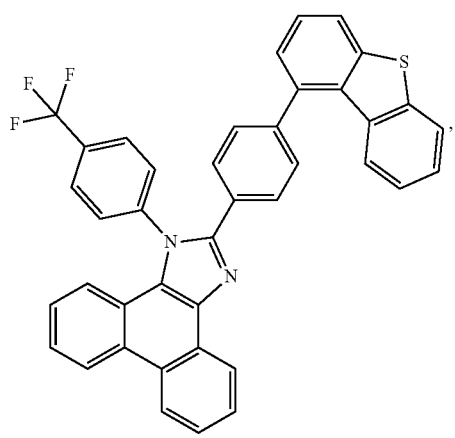
A4
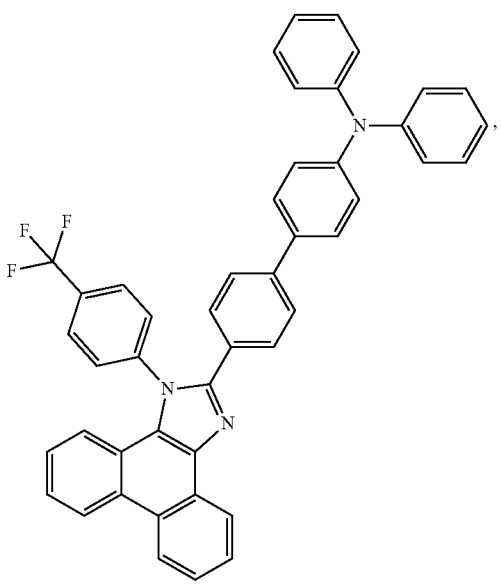
A21
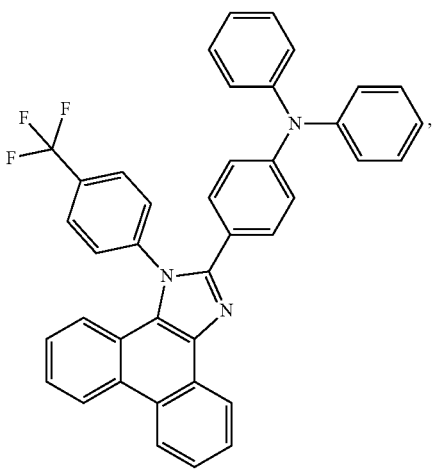
A23
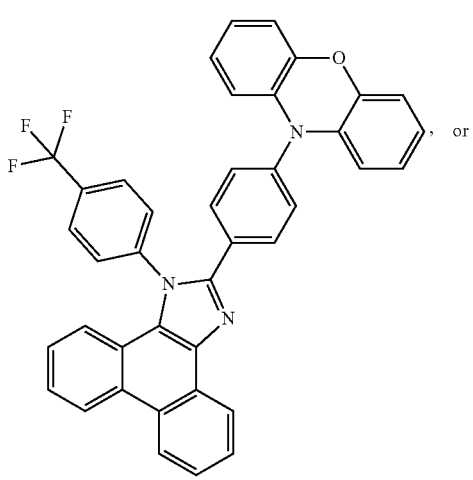
A26, or
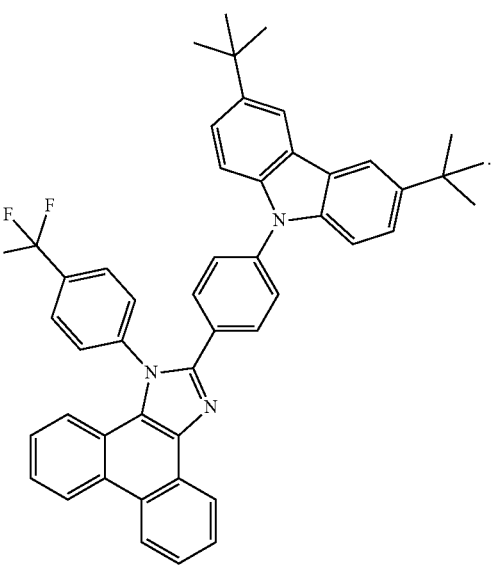
A39
A preparation method for the phenanthroimidazole derivative, including the steps of:
S1. dissolving 9,10-phenanthrenequinone, 4-trifluoromethyl aniline, 4-bromobenzaldehyde, and a catalyst in an organic solvent at 110 to 120° ° C. to obtain an intermediate product having a structure as shown in Formula (II),

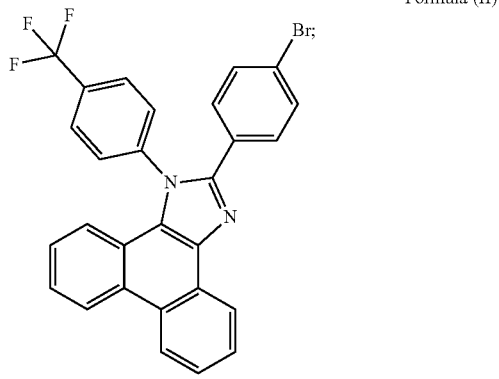

Formula (II)

S2. dissolving the intermediate product obtained by S1, a compound containing the above-mentioned electron donor group R, and a catalyst in an organic solvent, and substituting a bromine atom in the intermediate product obtained by S1 with the electron donor group R in the compound at 70 to 190° ° C. to obtain a phenanthroimidazole derivative having a structure as shown in Formula (I).

Preferably, the molar ratio of 9,10-phenanthrenequinone, 4-trifluoromethylaniline, 4-bromobenzaldehyde, ammonium acetate in S1 is 1-1.2:1-1.2:1-1.2:1-10.

Further preferably, the molar ratio of 9,10-phenanthrenequinone, 4-trifluoromethylaniline, 4-bromobenzaldehyde, ammonium acetate in S1 is 1:1:1:6.

Preferably, the catalyst in S1 is ammonium acetate.

Preferably, the organic solvent in S1 is acetic acid.

Preferably, the reaction in S1 is carried out in an inert atmosphere.

Further preferably, the inert atmosphere in S1 is an atmosphere consisting of one or more of nitrogen, helium, or argon.

Preferably, the temperature of the reaction in S1 is 120° C.

Preferably, the reaction time in S1 is from 6 to 8 h.

Preferably, after the completion of the reaction in S1 a post-treatment is further included, the post-treatment being successively extraction, distillation under reduced pressure, and separation and purification.

Preferably, in the compounds described in S2 which contain an electron donor group R as described above. R may be attached to a boronic acid group or a hydrogen atom.

Preferably, the catalyst in S2 is one or a combination of two of a basic salt or tetrakis triphenylphosphine palladium.

Further preferably, the basic salt is one or a combination of two of potassium carbonate or potassium tert-butoxide.

Preferably, the molar ratio of electron donor groups in the intermediate product, the basic salt, and the compound containing the above-mentioned electron donor group R in S2 is 1:1.5:(1-1.2).

Preferably, the organic solvent in S2 is any one of tetrahydrofuran, ortho-dichlorobenzene, or toluene.

Preferably, when the organic solvent in S2 is tetrahydrofuran, the temperature of the reaction in S2 is from 70 to 75° C.; when the organic solvent in S2 is ortho-dichlorobenzene, the temperature of the reaction in S2 is 180 to 190° C.; when the organic solvent in S2 is toluene, the temperature of the reaction in S2 is 110 to 120° ° C.

Preferably, the time of the reaction in S2 is from 10 to 16 h.

Preferably, after the completion of the reaction in S2 further including a post-treatment which is extraction, distillation under reduced pressure, separation and purification successively.

Preferably, the extractant is one or both of dichloromethane and saturated brine.

Preferably, the separation and purification are by silica gel column chromatography.

The use of the above phenanthroimidazole derivatives for the preparation of UV light-curing initiators is also within the scope of the present invention.

Compared to the prior art, the advantageous effects of the present invention are:

in the present invention, wherein by taking a phenanthroimidazole group containing a trifluoromethyl phenyl group as an electron acceptor, and in virtue of the properties of the specific electron donor group R, the phenanthroimidazole derivative containing a light-absorbing photosensitive group of a series D-π-A structure is synthesized and can be used as a photoinitiator, which is used in the technical field of UV light-curing systems or 3D printing. The phenanthroimidazole derivative has a certain conjugated chain length, can increase its photon absorption cross section, can serve as a photoinitiator of a UV light-curing system, for initiating a polymerization reaction at a wavelength of 365 nm, and has high polymerization efficiency; a double bond conversion rate of the phenanthroimidazole derivative in 50 s is up to 88.34%.

DESCRIPTION OF THE EMBODIMENTS

Figure 1:
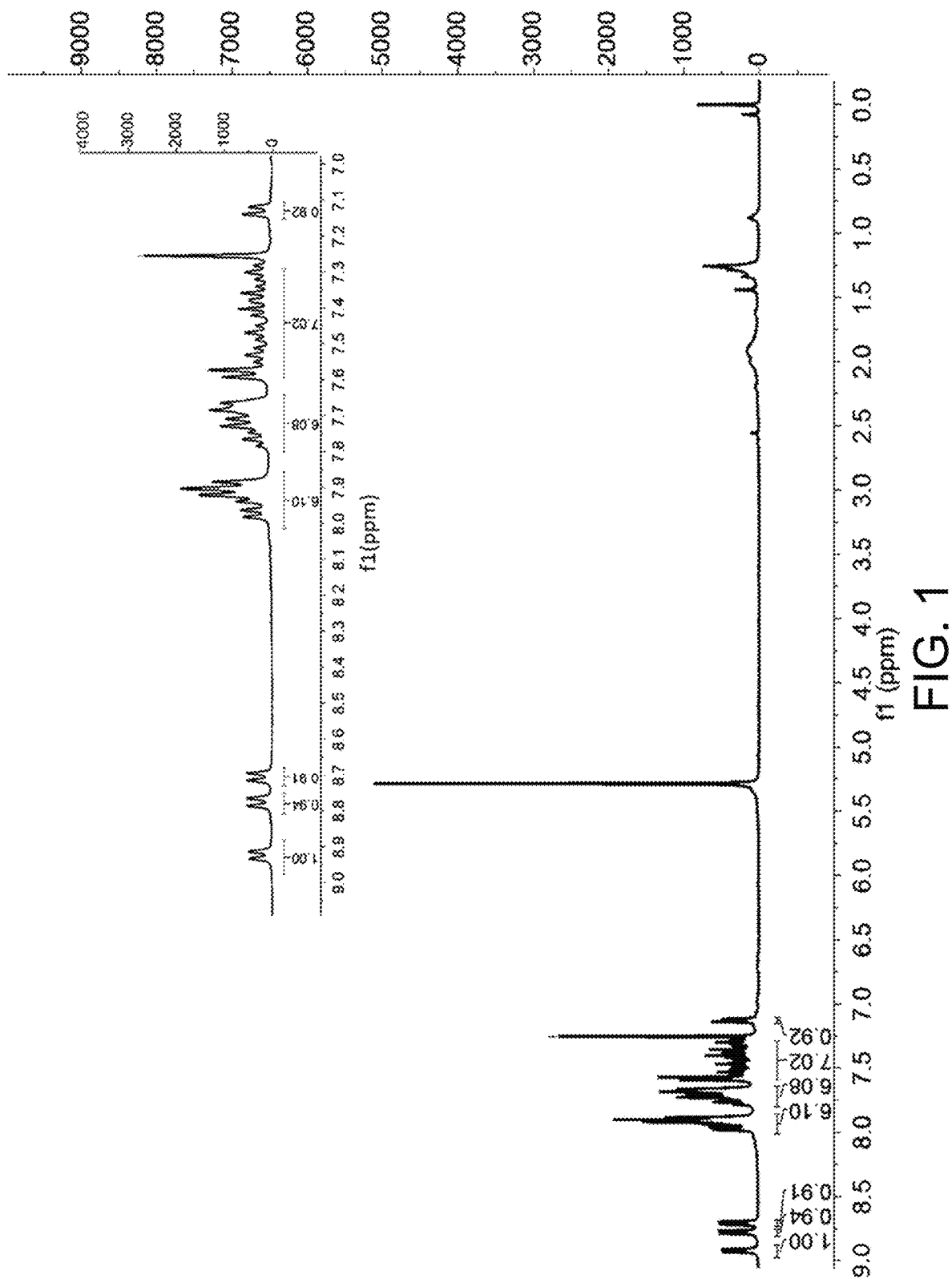
FIG. 1 is a ¹HMNR diagram of a phenanthroimidazole derivative A1 prepared in Example 1.

The invention will now be further described with reference to specific examples and drawings, which are not intended to limit the invention in any way. Unless otherwise indicated, the reagents, methods, and equipment used herein are those conventional in the art. Reagents and materials used in the present invention are commercially available unless otherwise specified.

Example 1

This example provides a phenanthroimidazole derivative as shown in Formula A1:

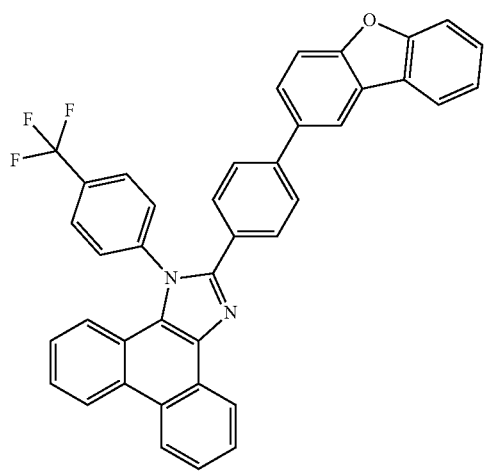

A1 the reaction equation and the preparation method for the compound are as follows:

reactant was heated to 120° C. and reacted for 8 h under the condition of nitrogen protection; after completion of the reaction, the reaction solution is cooled to room temperature, the reaction solution is extracted three times with dichloromethane and saturated brine (volume ratio is 1:1), the organic phase is taken and distilled under reduced pressure to obtain a crude product; after separation and purification by silica gel column chromatography with dichloromethane/petroleum ether as eluent, the phenanthroimidazole derivative containing trifluoromethyl phenyl group was obtained (with a yield of 77.27 mol %);

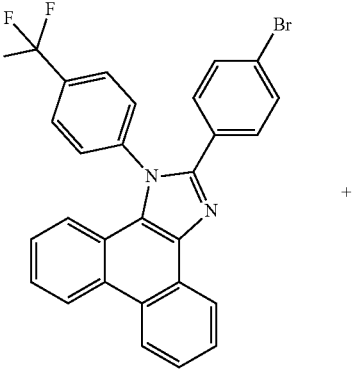

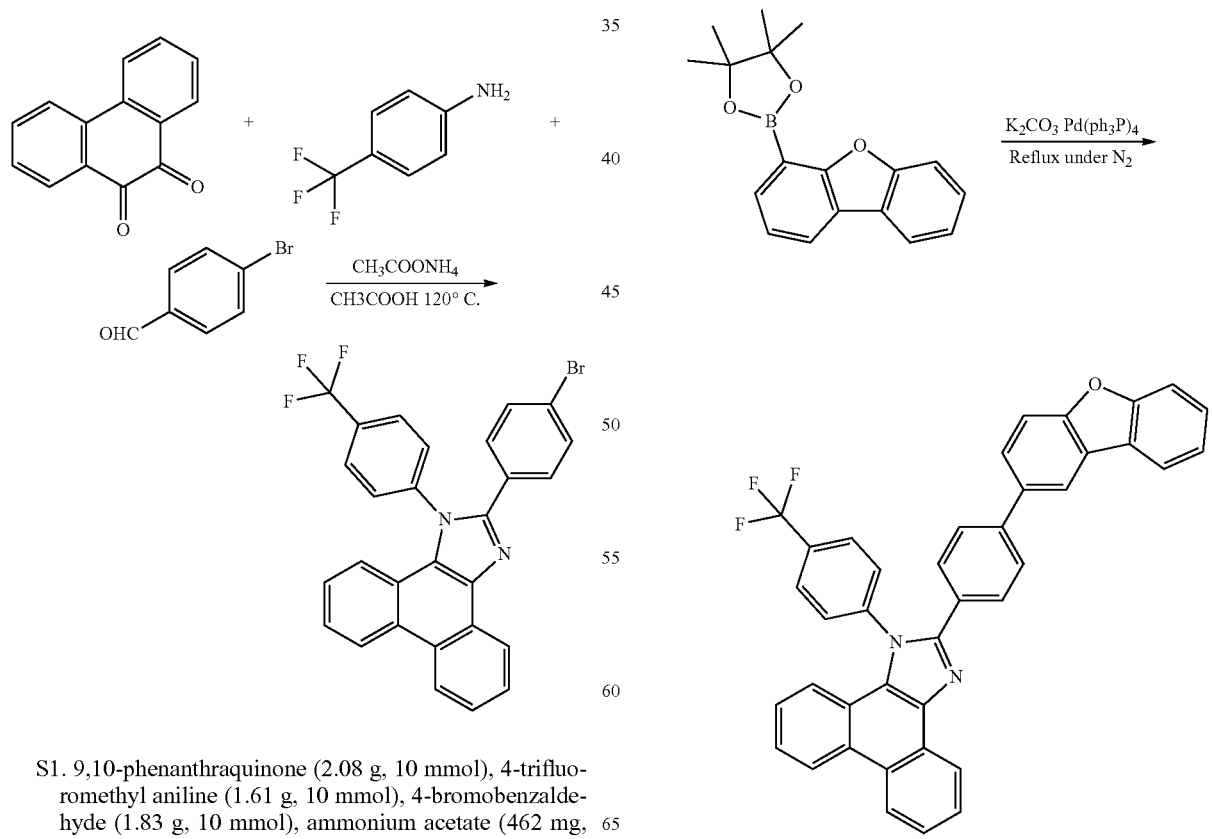

S1. 9,10-phenanthraquinone (2.08 g, 10 mmol), 4-trifluoromethyl aniline (1.61 g, 10 mmol), 4-bromobenzaldehyde (1.83 g, 10 mmol), ammonium acetate (462 mg, 60 mmol) were successively added to a 250 ml round bottom flask and dissolved in an acetic acid solvent; the S2. the product phenanthroimidazole derivative containing trifluoromethyl phenyl group (517 mg, 1 mmol) obtained in S1, dibenzo [b,d] furan-2-boronic acid (212 mg, 1 mmol), potassium carbonate (210 mg, 1.5 mmol) and tetrakis triphenylphosphine palladium (23 mg, 0.02 mmol) were successively added into a 250 mL round bottom flask and dissolved in a mixed solvent consisting of tetrahydrofuran and water; the reactant was heated to 120° C. and reacted for 12 h under the condition of nitrogen protection; after completion of the reaction, the reaction solution is cooled to room temperature, and extracted three times with dichloromethane and saturated brine; the organic phase is taken and distilled under reduced pressure to obtain a crude product; after separation and purification by silica gel column chromatography with dichloromethane/petroleum ether as eluent, the phenanthroimidazole derivative A1 was obtained (with a yield of 91.2 mol %).

Figure 2:
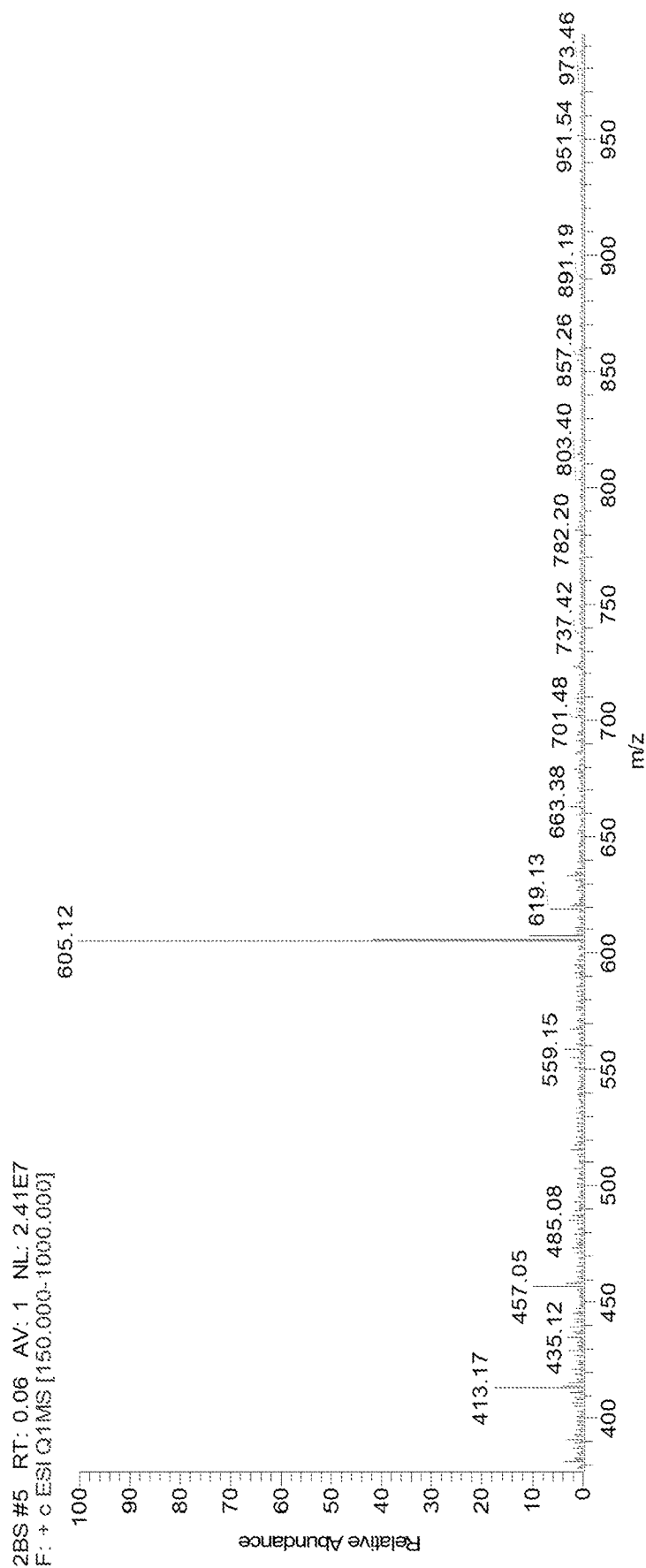
FIG. 2 is a mass spectrogram of the phenanthroimidazole derivative A1 prepared in Example 1.

The chemical structure of the prepared phenanthroimidazole derivative A1 was determined:

the structural formula was determined using a Bruker 400 MHz superconducting nuclear magnetic resonance instrument with deuterated chloroform as the solvent. The obtained hydrogen spectrum from determination was shown in FIG. 1 with the characteristic wave numbers (ppm) as $^1$H NMR (400 MHZ, Chloroform-d) δ8.92 (d, J=7.9 Hz, 1H), 8.78 (d, J=8.4 Hz, 1H), 8.71 (d, J=8.3 Hz, 1H), 8.01-7.86 (m, 6H), 7.72 (ddd, J=26.1, 11.6, 5.9 Hz, 6H), 7.59-7.29 (m, 7H), 7.13 (d, J=8.3 Hz, 1H). It can be seen that the wave peak of the molecular hydrogen spectrum is in one-to-one correspondence with the target product;

mass spectrometry: the phenanthroimidazole derivative A1 prepared in Example 1 was dissolved in dichloromethane to prepare a solution with a concentration of 1 mg/mL, and the mass spectrometry was performed using a liquid chromatography-mass spectrometry instrument LCMS-2020, and the test result is shown in FIG. 2. It can be obtained from the figure that the relative molecular mass of the phenanthroimidazole derivative A1 is 650.12, and subtracting one H is consistent with the relative molecular mass of the synthesized A1.

Ultraviolet absorption spectrum detection: Shimadzu UV-visible spectrophotometer UV-2700 was used, and the scanning range was 250 to 700 nm; A1 prepared in the examples was used as a novel photoinitiator under the coaction of an iodonium salt (specifically $C_{12}H_{10}F_6IP$) and initiates the polymerization of the monomer trimethylolpropane triacrylic acid under a 365 nm wavelength UV light source (the light intensity is 30 mw/cm$^2$) (the amount of A1 used was 1 wt % of the monomer; the amount of iodonium salt used was 1.5 wt % of the monomer). The results (see FIGS. 10 and 11) indicate that: the double bond conversion rate of A1 within 50 s was 88.34% (obtained by calculating the peak area change corresponding to the double bond by real-time infrared), which was 2.765 times higher than that of the conventional commercial initiator tertiary amine (the amount of tertiary amine/iodonium salt used was 1 wt % and 1.5 wt % of the monomer, respectively, and the double bond conversion rate was 32% under the same conditions).

Example 2

This example provides a phenanthroimidazole derivative as shown in Formula A4:

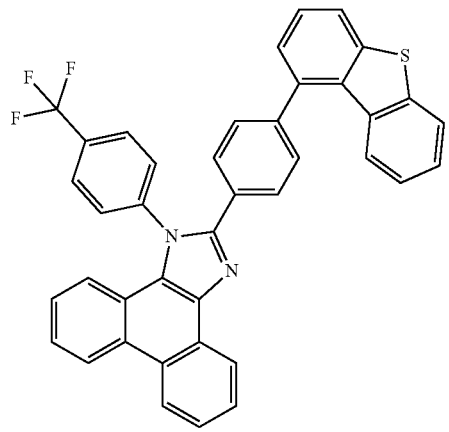

A4

Figure 3:
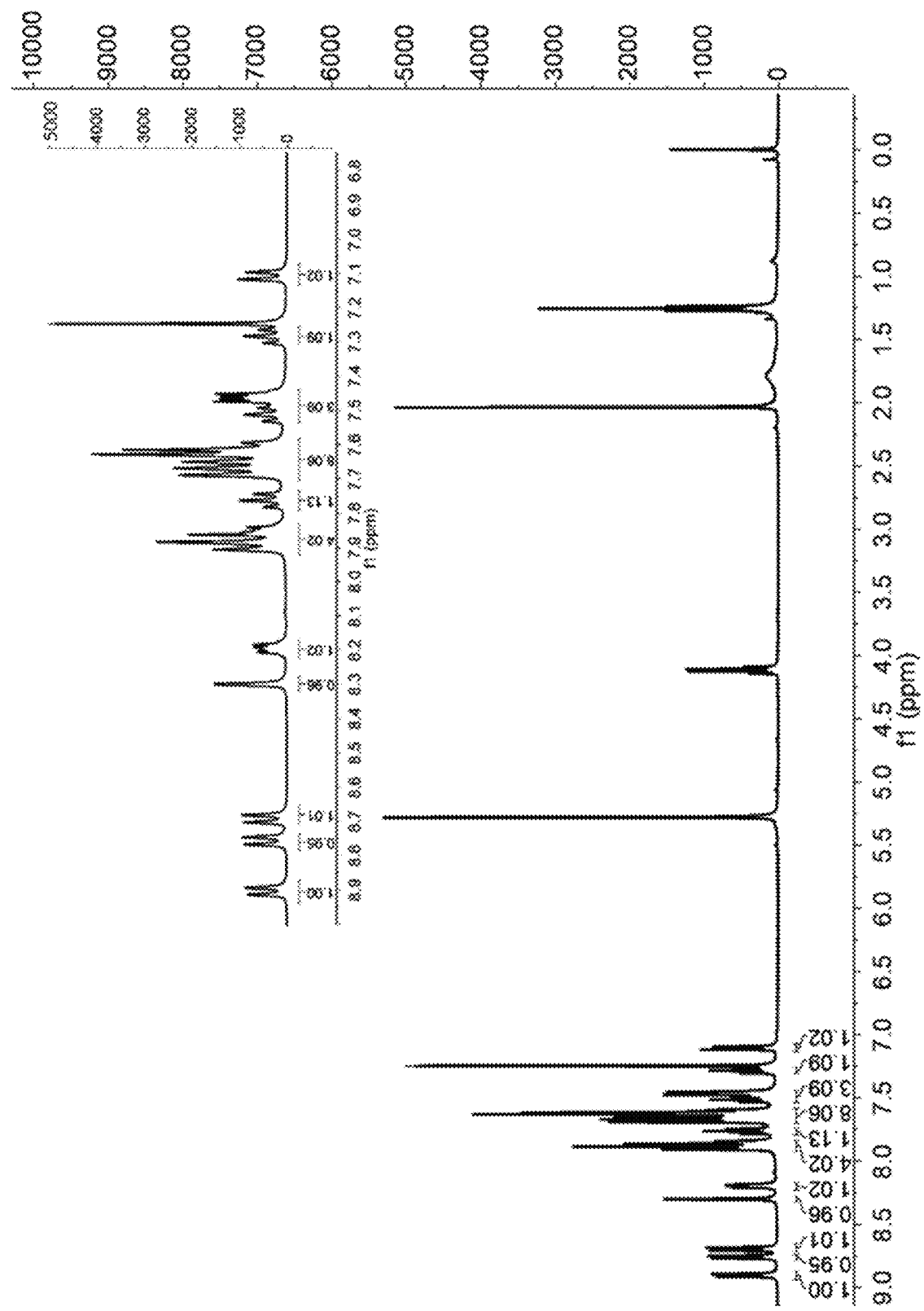
FIG. 3 is a ¹HMNR diagram of the phenanthroimidazole derivative A4 prepared in Example 2.
Figure 4:
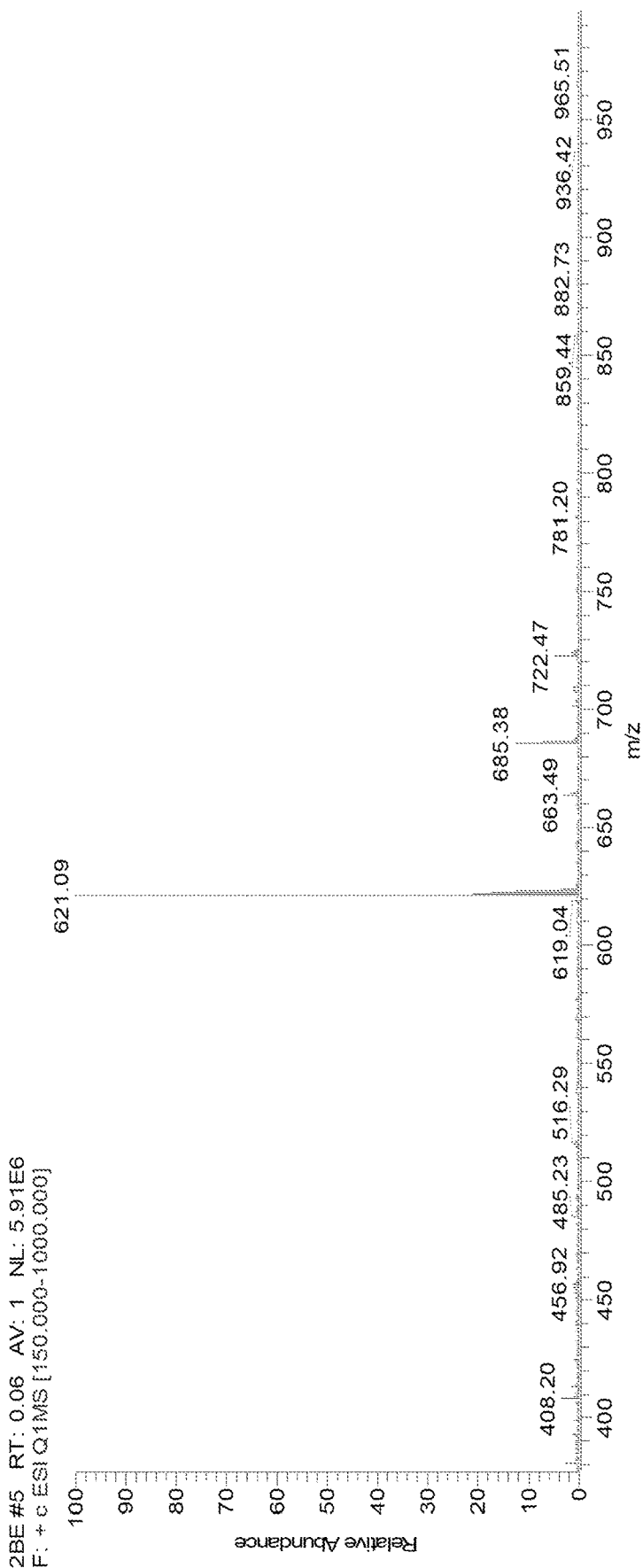
FIG. 4 is a mass spectrogram of the phenanthroimidazole derivative A4 prepared in Example 2.

This compound was prepared in a manner different from that of Example 1 in that dibenzo [b,d] furan-2-boronic acid (212 mg, 1 mmol) in S2 was replaced with dibenzothiophene 2-boronic acid (228 mg, 1 mmol) to finally prepare phenanthroimidazole derivative A4 in a yield of 81.82 mol %.

Where the characteristic wave numbers (ppm) of the nuclear magnetic hydrogen spectrum of A4 (see FIG. 3) was $^1$H NMR$^1$H NMR (400 MHZ, Chloroform-d) δ8.90 (dd, J=7.9, 1.4 Hz, 1H), 8.76 (d, J=8.4 Hz, 1H), 8.69 (d, J=8.3 Hz, 1H), 8.30 (d, J=1.8 Hz, 1H), 8.19 (dt, J=7.3, 3.6 Hz, 1H), 7.92-7.83 (m, 4H), 7.76 (t, J=7.3 Hz, 1H), 7.70-7.58 (m, 8H), 7.54-7.44 (m, 3H), 7.31-7.26 (m, 1H), 7.13-7.07 (m, 1H); mass spectrometry (FIG. 4) analysis of A4 gave a relative molecular weight of 621.09; UV light absorption detection (the specific conditions were the same as those in Example 1, see FIG. 10), and the result (see FIG. 11) shows that the double bond conversion rate of A4 in 50 s is 65.35%, which is 2.05 times of that of tertiary amine/iodonium salt of traditional commercial initiator.

Example 3

This example provides a phenanthroimidazole derivative as shown in Formula A21:

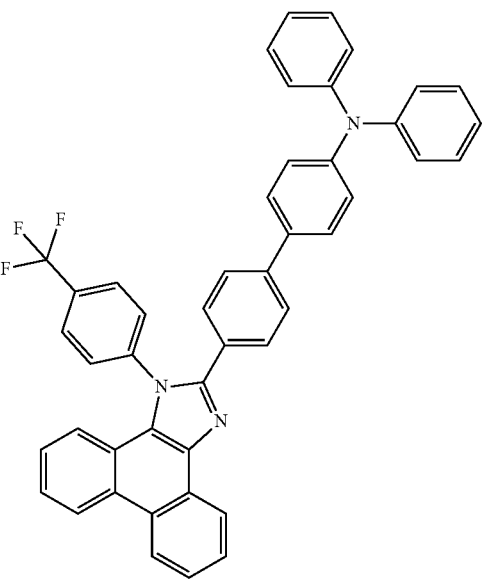

A21

Figure 5:
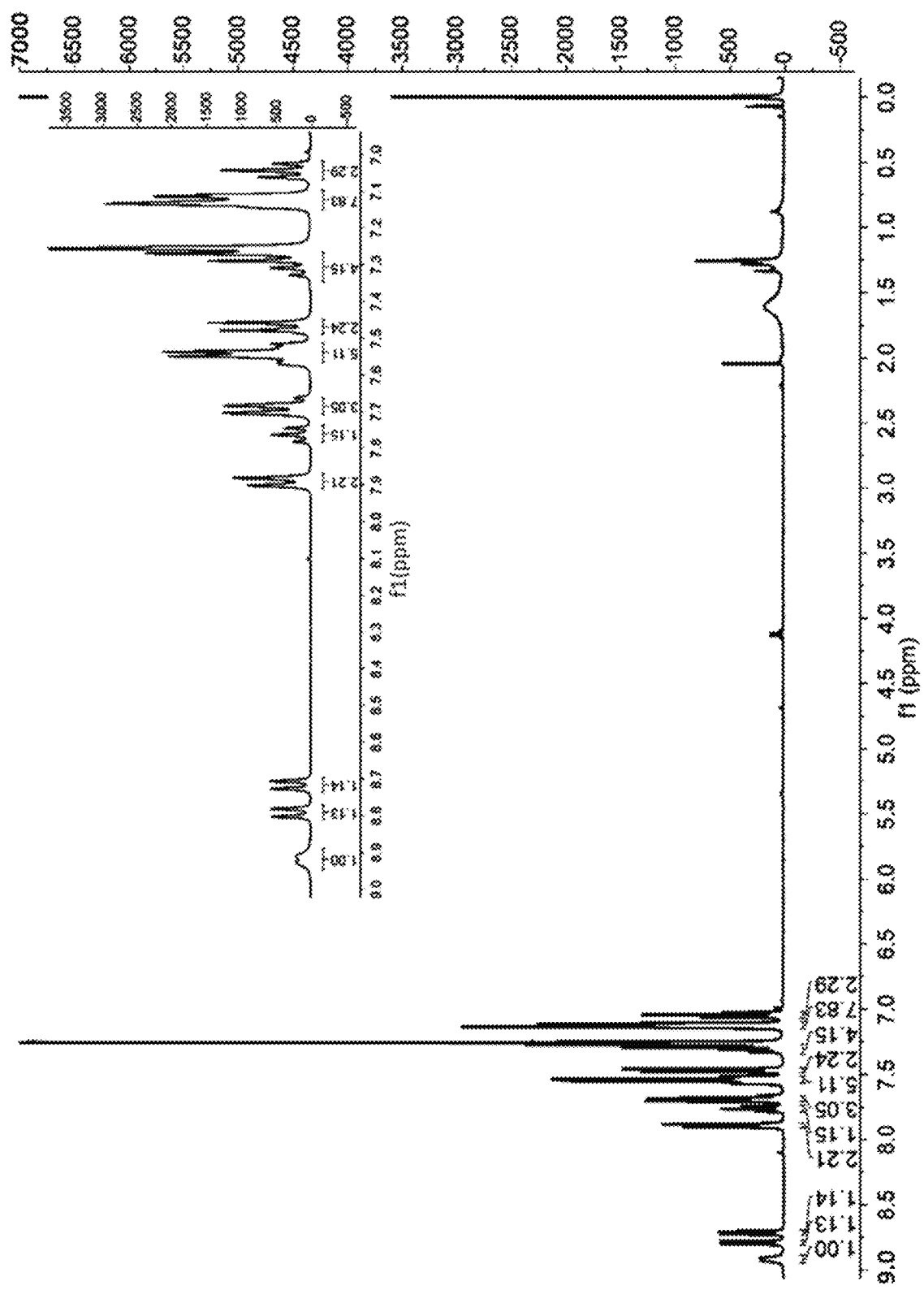
FIG. 5 is a ¹HMNR diagram of a phenanthroimidazole derivative A21 prepared in Example 3.
Figure 6:
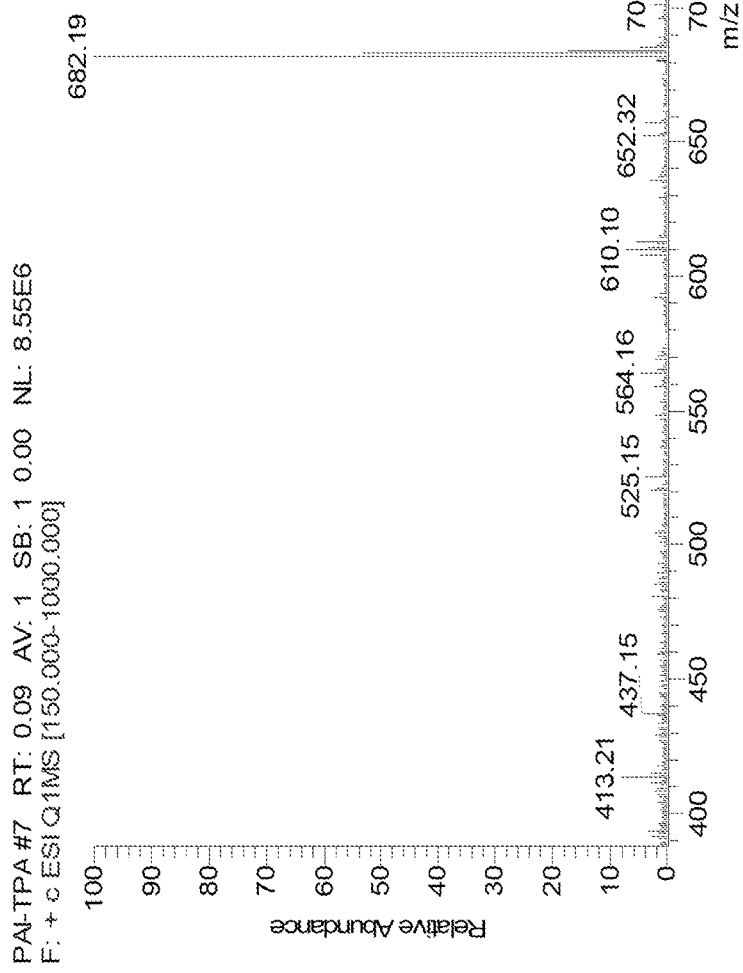
FIG. 6 is a mass spectrogram of the phenanthroimidazole derivative A21 prepared in Example 3.

This compound was prepared in a manner different from that of Example 1 in that dibenzo [b,d] furan-2-boronic acid (212 mg, 1 mmol) in S2 was replaced with triphenylamine 4-boronic acid (289 mg, 1 mmol) to finally prepare phenanthroimidazole derivative A21 in a yield of 76.42 mol %.

Where the characteristic wave numbers (ppm) of the nuclear magnetic hydrogen spectrum of A21 (see FIG. 5) was $^1$H NMR (400 MHZ, Chloroform-d) δ8.92 (d, J=7.9 Hz, 1H), 8.79 (d, J=8.4 Hz, 1H), 8.72 (d, J=8.3 Hz, 1H), 7.89 (d, J=8.1 Hz, 2H), 7.78-7.74 (m, 1H), 7.71-7.66 (m, 3H), 7.56-7.51 (m, 5H), 7.49-7.45 (m, 2H), 7.35-7.27 (m, 4H), 7.13 (dtd, J=9.2, 4.8, 4.1, 2.1 Hz, 8H), 7.04 (tt, J=7.1, 1.2 Hz, 2H); mass spectrometry (FIG. 6) analysis of A21 gave a relative molecular weight of 682.19; UV light absorption detection (the specific conditions were the same as those in Example 1, see FIG. 10), and the result (see FIG. 11) shows that the double bond conversion rate of A21 in 50 s is 60.47%, which is 1.89 times of that of tertiary amine/iodonium salt of traditional commercial initiator.

Example 4

This example provides a phenanthroimidazole derivative as shown in Formula A39:

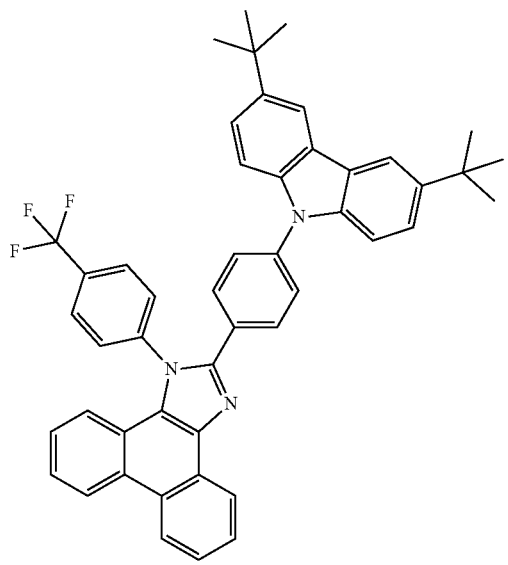

A39

Figure 7:
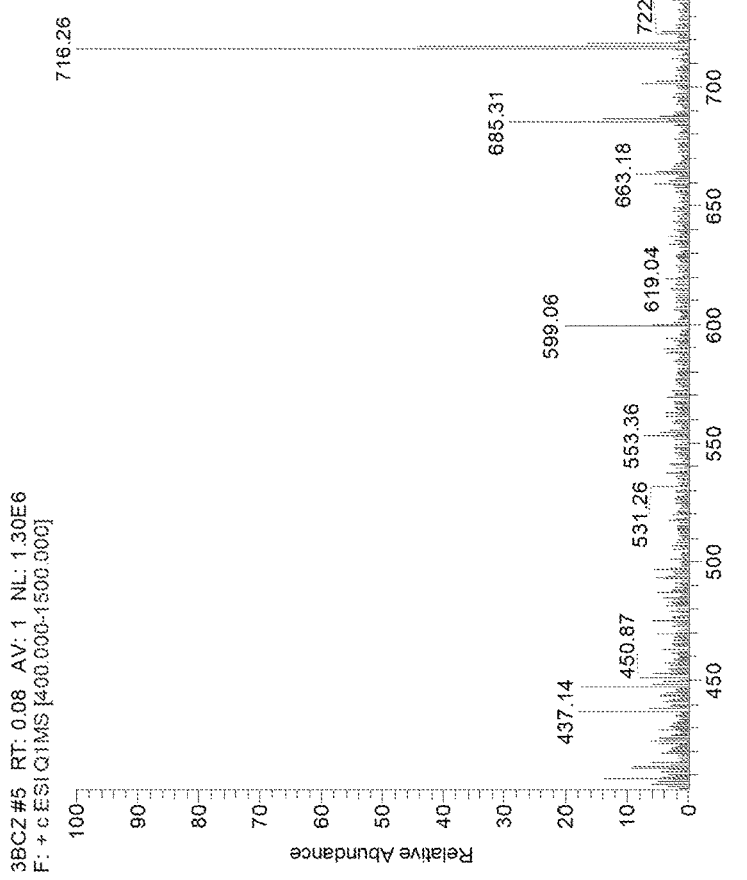
FIG. 7 is a mass spectrogram of the phenanthroimidazole derivative A39 prepared in Example 4.
Figure 10:
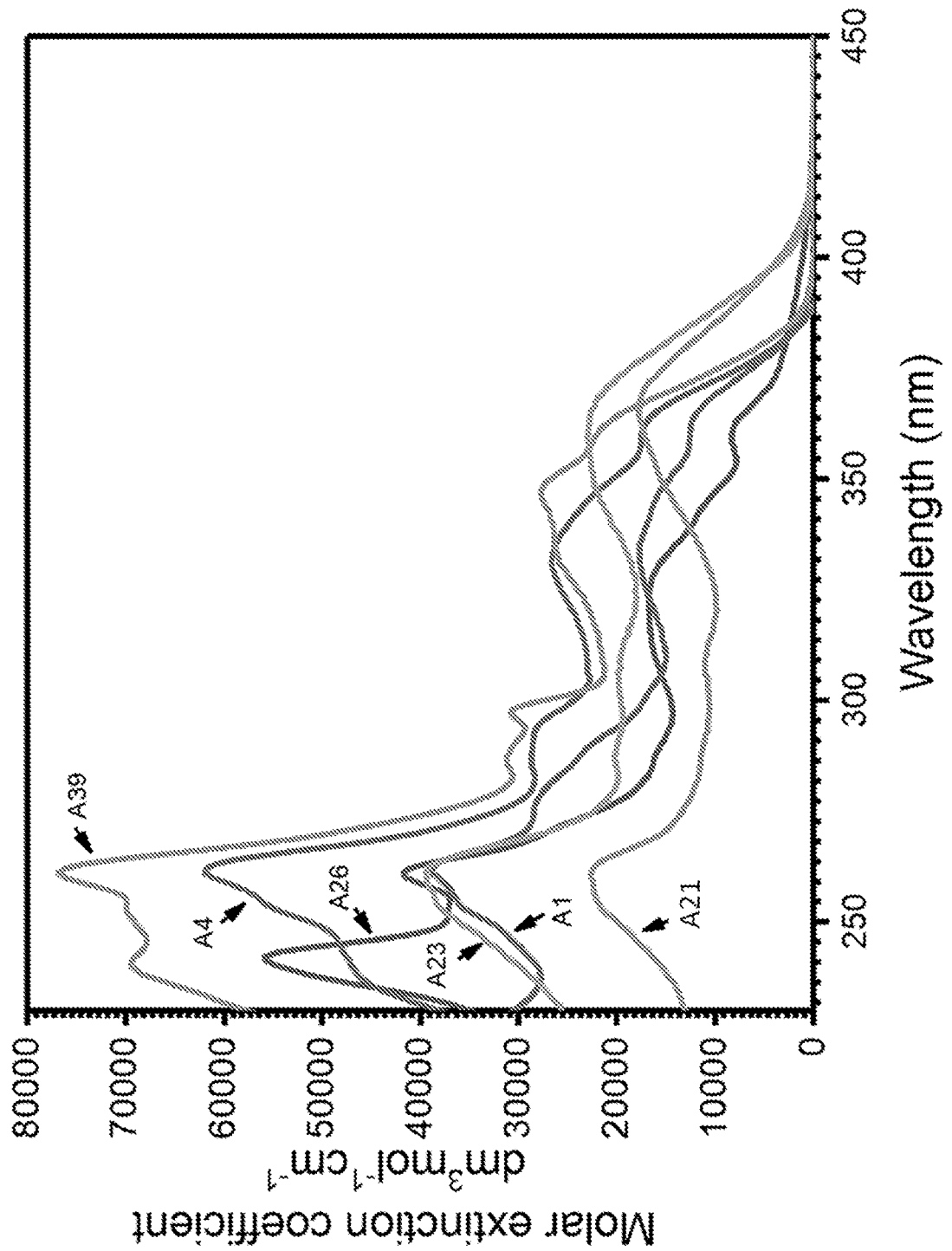
FIG. 10 is a graph showing UV absorption of phenanthroimidazole derivatives A1, A4, A21, A23, A26, and A39 prepared in Examples in a dichloromethane solution.
Figure 11:
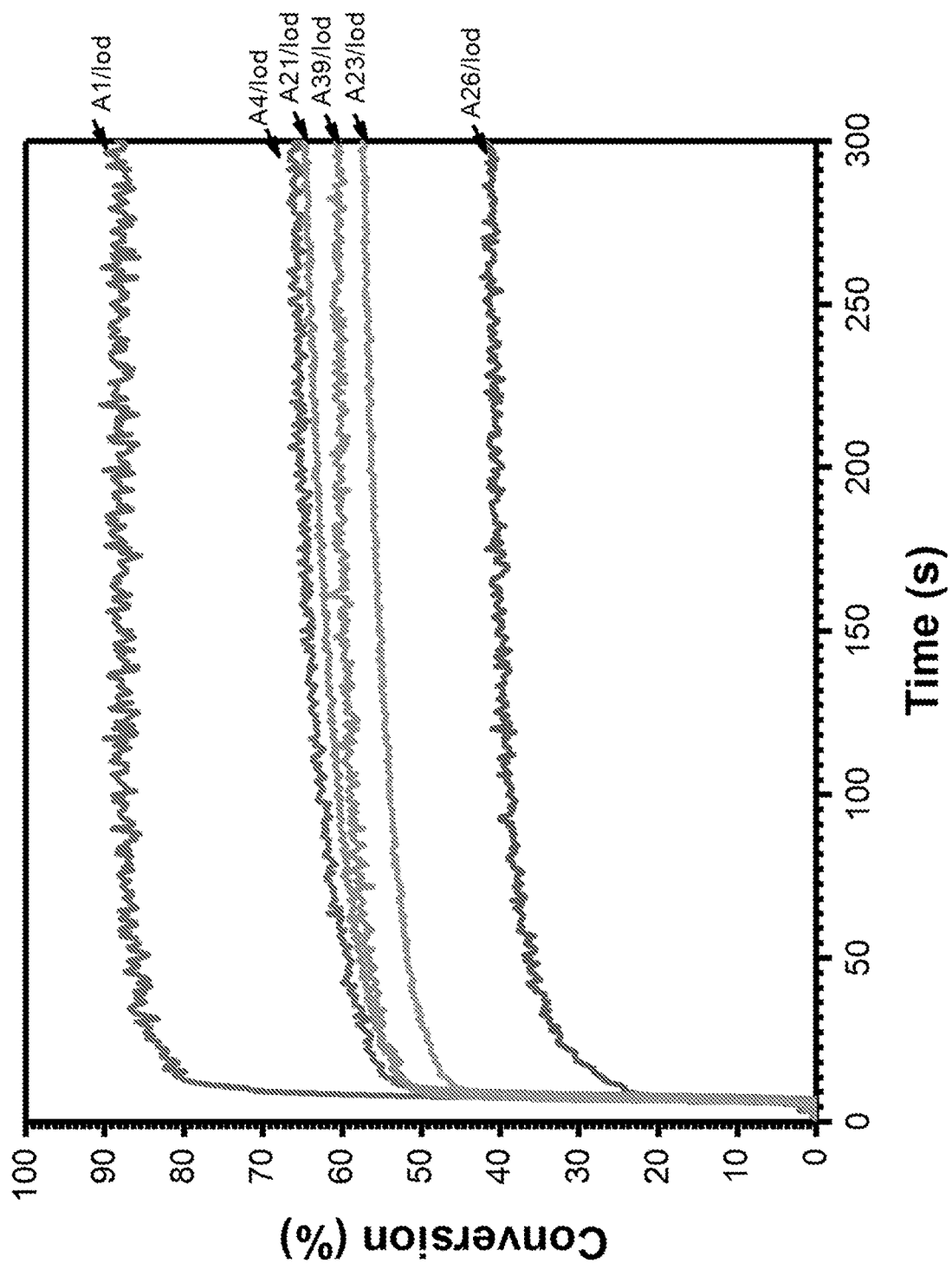
FIG. 11 is a graph showing double bond conversion rates of phenanthroimidazole derivatives A1, A4, A21, A23, A26, and A39 prepared in Examples as photoinitiators in combination with iodonium salts.

This compound was prepared in a manner different from that of Example 1 in that dibenzo [b,d] furan-2-boronic acid (212 mg, 1 mmol) in S2 was replaced with 3,6-tert-butyl-carbazole (279 mg, 1 mmol) to finally prepare phenanthro-imidazole derivative A39 in a yield of 22.37 mol %.

Where the characteristic wave numbers (ppm) of the nuclear magnetic hydrogen spectrum of A39 was $^1$H NMR (400 MHZ, Chloroform-d) δ9.08 (s, 1H), 8.15 (d, J=2.0 Hz, 2H), 7.98 (d, J=8.8 Hz, 1H), 7.78 (qq, J=15.5, 7.6, 6.4 Hz, 4H), 7.58 (dd, J=8.5, 4.3 Hz, 2H), 7.49 (d, J=9.0 Hz, 1H), 7.39-7.32 (m, 1H), 7.31-7.27 (m, 11H), 7.26 (s, 1H), 7.18 (d, J=8.7 Hz, 1H), 7.12 (s, 1H), 5.34-5.29 (m, 4H), 1.36 (s, 1H), 1.31 (d, J=1.3 Hz, 1H), 1.28 (s, 13H), 0.93-0.86 (m, 1H); mass spectrometry (FIG. 7) analysis of A39 gave a relative molecular weight of 716.26;

the UV light absorption detection (the specific conditions were the same as those in Example 1, see FIG. 10), and the result (see FIG. 11) shows that the double bond conversion rate of A39 in 50 s is 64.8%, which is 2.025 times of that of tertiary amine/iodonium salt of a traditional commercial initiator.

Example 5

This example provides a phenanthroimidazole derivative as shown in Formula A23:

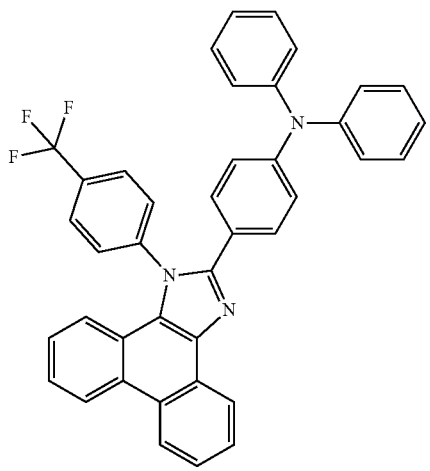

A23

This compound was prepared in a manner different from that of Example 1 in that dibenzo [b,d] furan-2-boronic acid (212 mg, 1 mmol) in S2 was replaced with diphenylamine (169 mg, 1 mmol) to finally prepare phenanthroimidazole derivative A23 in a yield of 32.36 mol %.

Figure 8:
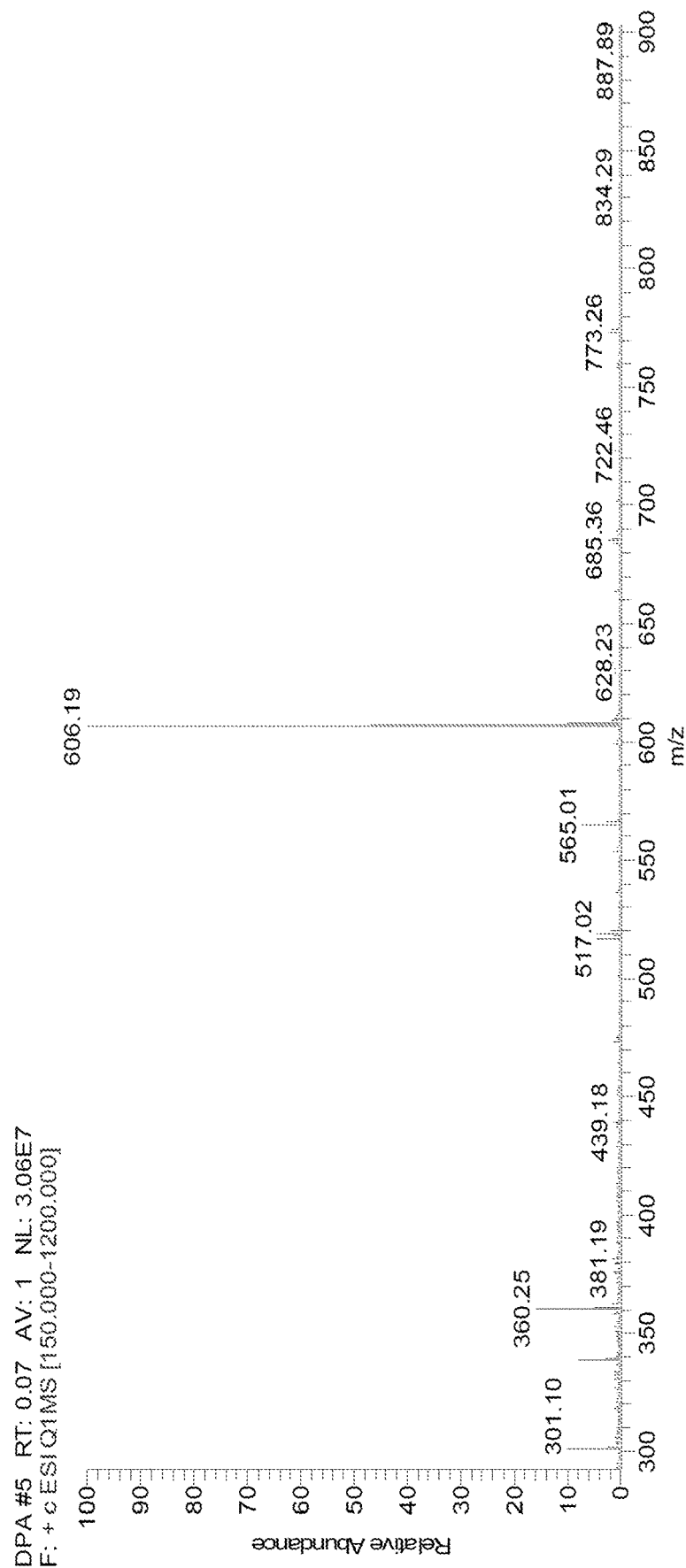
FIG. 8 is a mass spectrogram of the phenanthroimidazole derivative A23 prepared in Example 5.

Wherein, the characteristic wave numbers (ppm) of the nuclear magnetic hydrogen spectrum of A23 was $^1$H NMR (400 MHZ, Chloroform-d) δ8.80 (d, J=8.5 Hz, 1H), 8.71 (d, J=8.3 Hz, 1H), 7.91 (t, J=9.0 Hz, 2H), 7.80-7.65 (m, 4H), 7.57 (t, J=7.6 Hz, 1H), 7.44 (dt, J=14.0, 7.1 Hz, 2H), 7.30 (d, J=8.0 Hz, 4H), 7.08 (dd, J=18.8, 9.1 Hz, 5H), 6.94 (d, J=8.6 Hz, 2H); mass spectrometry (FIG. 8) analysis of A23 gave a relative molecular weight of 606.19;

the UV light absorption detection (the specific conditions were the same as those in Example 1, see FIG. 10), and the result (see FIG. 11) shows that the double bond conversion rate of A23 in 50 s is 57.18%, which is 1.78 times of that of tertiary amine/iodonium salt of a traditional commercial initiator.

Example 6

This example provides a phenanthroimidazole derivative as shown in Formula A26:

A26

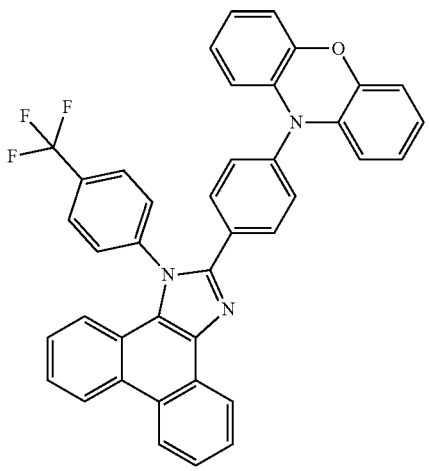

This compound was prepared in a manner different from that of Example 1 in that dibenzo [b,d] furan-2-boronic acid (212 mg, 1 mmol) in S2 was replaced with phenoxazine (183 mg, 1 mmol) to finally prepare phenanthroimidazole derivative A26 in a yield of 67.2 mol %.

Figure 9:
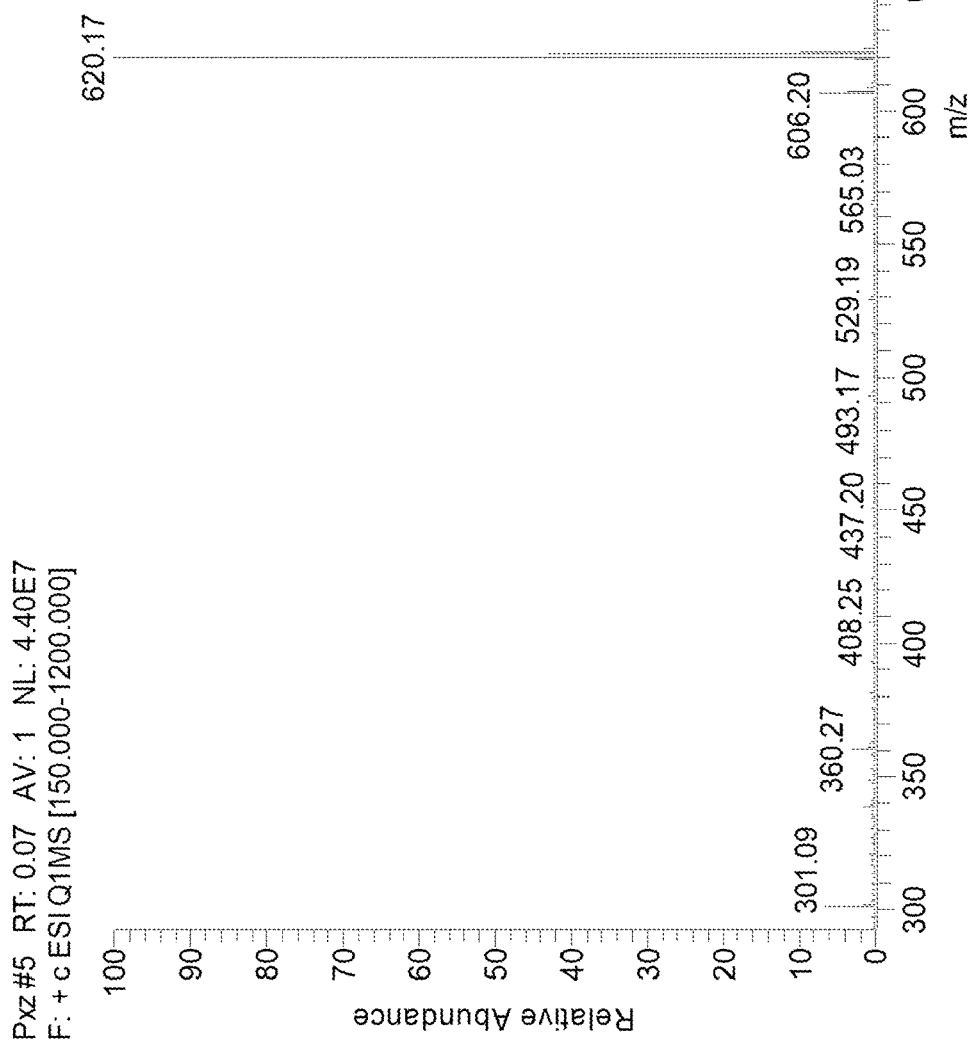
FIG. 9 is a mass spectrogram of the phenanthroimidazole derivative A26 prepared in Example 6.

Wherein, the characteristic wave numbers (ppm) of the nuclear magnetic hydrogen spectrum of A26 was $^1$H NMR (400 MHZ, Chloroform-d) δ8.93 (s, 1H), 8.81 (d, J=8.4 Hz, 1H), 8.74 (d, J=8.3 Hz, 1H), 7.93 (d, J=8.2 Hz, 2H), 7.82-7.67 (m, 6H), 7.58 (ddd, J=8.4, 7.0, 1.3 Hz, 1H), 7.38-7.28 (m, 3H), 7.15 (dd, J=8.4, 1.3 Hz, 1H), 6.74-6.52 (m, 6H), 5.90 (s, 2H); mass spectrometry (FIG. 9) analysis of A26 gave a relative molecular weight of 620.17;

the UV light absorption detection (the specific conditions were the same as those in Example 1, see FIG. 10), and the result (see FIG. 11) shows that the double bond conversion rate of A23 in 50 s is 41.42%, which is 1.29 times of that of tertiary amine/iodonium salt of a traditional commercial initiator.

The above-described embodiments further illustrate the objects, technical solutions, and advantages of the present invention. It should be understood that the foregoing description is only illustrative of specific embodiments of the present invention, and is not intended to limit the scope of the invention. It is intended that the invention be construed as including all such modifications and alterations insofar as they come within the scope of the appended claims or the equivalents thereof.

What is claimed is:

1. A phenanthroimidazole-derivative, having a structural formula as Formula (I):

Formula (I)

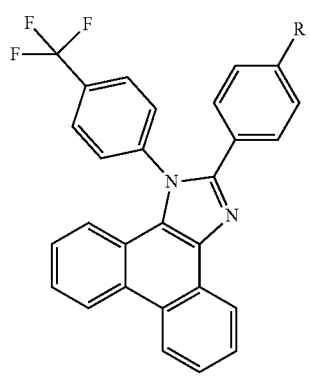

in the Formula (I), R is selected from

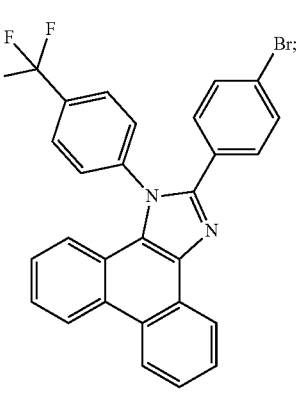

2. A preparation method for the phenanthroimidazole of claim 1, comprising the following steps of:

S1. dissolving 9,10-phenanthrenequinone, 4-trifluoromethyl aniline, 4-bromobenzaldehyde, and ammonium acetate in an organic solvent at 110 to 120° C. to obtain an intermediate product having a structure as shown in Formula (II), Formula (II)

S2. dissolving the intermediate product obtained by S1, a compound containing the R of claim 1, and a catalyst in an organic solvent, and substituting a bromine atom in the intermediate product obtained by S1 with the R in the compound at 70 to 190° C. to obtain the phenanthroimidazole having a structure as shown in Formula (I);

wherein, the compound containing the R as claimed in claim 1 in step S2 is R-boric acid or R—H.

3. The preparation method for the phenanthroimidazole of claim 2, wherein in S1, the molar ratio of 9,10-phenanthraquinone, 4-trifluoromethyl aniline, 4-bromobenzaldehyde and ammonium acetate is 1-1.2:1-1.2:1-1.2:1-10.

4. The preparation method for the phenanthroimidazole of claim 2, wherein in S2, the molar ratio of the intermediate product, the catalyst, and the R of claim 1 is 1:1.5:1-1.2.

5. The preparation method for the phenanthroimidazole of claim 2, wherein the catalyst in S2 is one of or a combination of two of basic salt and tetrakis triphenylphosphine palladium.

6. The preparation method for the phenanthroimidazole of claim 2, wherein the organic solvent in S1 is acetic acid; the organic solvent in S2 is any one of tetrahydrofuran, ortho-dichlorobenzene, and toluene.

* * * * *